United States Patent
Pedro et al.

(10) Patent No.: US 12,076,485 B2
(45) Date of Patent: *Sep. 3, 2024

(54) VENTILATION MASK

(71) Applicant: SunMed Group Holdings, LLC, Grand Rapids, MI (US)

(72) Inventors: Michael J. Pedro, Windham, NH (US); Thomas M. Reilly, Tucson, AZ (US); Ryan G. Redford, Tucson, AZ (US); David M. Kane, Tucson, AZ (US)

(73) Assignee: SunMed Group Holdings, LLC, Grand Rapids, MI (US)

(*) Notice: Subject to any disclaimer, the term of this patent is extended or adjusted under 35 U.S.C. 154(b) by 239 days.

This patent is subject to a terminal disclaimer.

(21) Appl. No.: 17/572,494

(22) Filed: Jan. 10, 2022

(65) Prior Publication Data

US 2022/0126047 A1 Apr. 28, 2022

Related U.S. Application Data

(63) Continuation of application No. 16/333,215, filed as application No. PCT/US2017/048046 on Aug. 22, 2017, now Pat. No. 11,298,492.

(Continued)

(51) Int. Cl.
*A61M 16/06* (2006.01)
*A61B 5/083* (2006.01)
(Continued)

(52) U.S. Cl.
CPC ......... *A61M 16/0616* (2014.02); *A61B 5/097* (2013.01); *A61M 16/085* (2014.02);
(Continued)

(58) Field of Classification Search
CPC .. A61M 16/00; A61M 16/06; A61M 16/0605; A61M 16/0611; A61M 16/0616;
(Continued)

(56) References Cited

U.S. PATENT DOCUMENTS

| | | | |
|---|---|---|---|
| 1,050,621 A | 1/1913 | Ford |
| 1,131,802 A | 3/1915 | Stenshoel |

(Continued)

FOREIGN PATENT DOCUMENTS

| | | |
|---|---|---|
| CN | 202478364 | 10/2012 |
| CN | 202505937 | 10/2012 |

(Continued)

OTHER PUBLICATIONS

Australian Certificate of Registration issued in application No. 201512961, dated Aug. 7, 2015, 5 pages.

(Continued)

*Primary Examiner* — Joseph D. Boecker
(74) *Attorney, Agent, or Firm* — Sheridan Ross P.C.

(57) ABSTRACT

A nasal mask has exhalation scoop fixed adjacent a lower portion of mask, adapted to overlie an upper lip of a patient when the mask is worn. The mask includes ports for sampling flow of $CO_2$ expelled from the mouth and nose of (Continued)

the patient to the end-tidal CO$_2$ port, and a pressure-based flow resistor for balancing flow of CO$_2$ expelled from the mouth and the nose of the patient.

17 Claims, 12 Drawing Sheets

Related U.S. Application Data

(60) Provisional application No. 62/510,192, filed on May 23, 2017, provisional application No. 62/467,808, filed on Mar. 6, 2017, provisional application No. 62/425,371, filed on Nov. 22, 2016, provisional application No. 62/394,405, filed on Sep. 14, 2016.

(51) Int. Cl.
| | |
|---|---|
| *A61B 5/097* | (2006.01) |
| *A61M 16/01* | (2006.01) |
| *A61M 16/08* | (2006.01) |
| *A61M 16/12* | (2006.01) |
| *A61M 16/20* | (2006.01) |
| *A61B 5/00* | (2006.01) |

(52) U.S. Cl.
CPC ......... *A61M 16/208* (2013.01); *A61B 5/0836* (2013.01); *A61B 5/6803* (2013.01); *A61M 16/01* (2013.01); *A61M 16/12* (2013.01); *A61M 2202/0208* (2013.01); *A61M 2202/0225* (2013.01); *A61M 2230/432* (2013.01)

(58) Field of Classification Search
CPC ......... A61M 16/0622; A61M 16/0666; A61M 16/0672; A61M 16/085; A61M 16/12; A61M 16/208; A61M 2202/0225; A61B 5/082; A61B 5/0836; A61B 5/097
See application file for complete search history.

(56) References Cited

U.S. PATENT DOCUMENTS

| | | | |
|---|---|---|---|
| 1,441,817 A | 1/1923 | McCullough | |
| 1,729,525 A | 9/1929 | Stenshoel | |
| 1,776,167 A | 9/1930 | Stenshoel | |
| 2,452,816 A | 11/1948 | Wagner | |
| 2,843,121 A | 7/1958 | Hudson | |
| 2,939,458 A | 6/1960 | Lundquist | |
| 3,013,556 A | 12/1961 | Galleher | |
| 3,522,612 A | 8/1970 | Palmer | |
| 3,556,097 A | 1/1971 | Wallace | |
| 3,799,164 A | 3/1974 | Rollins | |
| 3,815,596 A | 6/1974 | Keener et al. | |
| 3,856,051 A | 12/1974 | Bain | |
| 3,889,668 A | 6/1975 | Ochs et al. | |
| 3,897,777 A | 8/1975 | Morrison | |
| D242,490 S | 11/1976 | Belkin | |
| 4,005,499 A | 2/1977 | Klein | |
| 4,007,737 A | 2/1977 | Paluch | |
| 4,015,598 A | 4/1977 | Brown | |
| 4,188,946 A | 2/1980 | Watson et al. | |
| D256,161 S | 7/1980 | Oliver | |
| 4,231,363 A | 11/1980 | Grimes | |
| 4,232,667 A | 11/1980 | Chalon et al. | |
| 4,248,218 A | 2/1981 | Fischer | |
| 4,259,757 A | 4/1981 | Watson | |
| 4,265,235 A | 5/1981 | Fukunaga | |
| 4,265,239 A | 5/1981 | Fischer, Jr et al. | |
| 4,275,720 A | 6/1981 | Wichman | |
| 4,328,797 A | 5/1982 | Rollins | |
| 4,457,026 A | 7/1984 | Morris | |
| 4,463,755 A | 8/1984 | Suzuki | |
| 4,471,769 A | 9/1984 | Lockhart | |
| 4,574,796 A | 3/1986 | Lundstrom | |
| 4,596,246 A | 6/1986 | Lyall | |
| 4,657,010 A | 4/1987 | Wright | |
| 4,677,977 A | 7/1987 | Wilcox | |
| 4,700,691 A | 10/1987 | Tari et al. | |
| 4,770,169 A | 9/1988 | Schmoegner et al. | |
| 4,895,172 A * | 1/1990 | Lindkvist ............ | A61M 16/009 128/863 |
| 4,905,712 A | 3/1990 | Bowlin et al. | |
| 5,046,200 A | 9/1991 | Feder | |
| 5,046,491 A | 9/1991 | Derrick | |
| 5,121,746 A | 6/1992 | Sikora | |
| D333,404 S | 2/1993 | Thompson | |
| 5,243,971 A | 9/1993 | Sullivan et al. | |
| 5,255,303 A | 10/1993 | DiMaio et al. | |
| 5,271,390 A | 12/1993 | Gray et al. | |
| 5,284,160 A | 2/1994 | Dryden | |
| D347,494 S | 5/1994 | Mustelier | |
| D354,128 S | 1/1995 | Rinehart | |
| 5,404,873 A | 4/1995 | Leagre et al. | |
| 5,462,050 A | 10/1995 | Dahlstrand | |
| 5,474,060 A | 12/1995 | Evans | |
| 5,485,837 A | 1/1996 | Solesbee et al. | |
| 5,524,639 A | 6/1996 | Lanier et al. | |
| D373,921 S | 9/1996 | Palomo et al. | |
| 5,557,049 A | 9/1996 | Ratner | |
| RE35,339 E | 10/1996 | Rapoport | |
| 5,560,354 A | 10/1996 | Berthon-Jones et al. | |
| 5,586,551 A | 12/1996 | Hilliard | |
| 5,647,357 A | 7/1997 | Barnett et al. | |
| 5,649,331 A | 7/1997 | Wilkinson et al. | |
| 5,660,174 A | 8/1997 | Jacobelli | |
| 5,661,859 A | 9/1997 | Schaefer | |
| 5,685,298 A | 11/1997 | Idris | |
| 5,738,094 A | 4/1998 | Hoftman | |
| 5,746,201 A | 5/1998 | Kidd | |
| 5,749,358 A | 5/1998 | Good et al. | |
| 5,778,872 A | 7/1998 | Fukunaga et al. | |
| D402,755 S | 12/1998 | Kwok | |
| 5,884,624 A | 3/1999 | Barnett et al. | |
| 5,933,886 A | 8/1999 | Washington | |
| 5,966,763 A | 10/1999 | Thomas et al. | |
| 5,975,079 A | 11/1999 | Hellings et al. | |
| 5,983,896 A | 11/1999 | Fukunaga et al. | |
| 6,003,511 A | 12/1999 | Fukunaga et al. | |
| 6,019,101 A | 2/2000 | Cotner et al. | |
| 6,035,852 A | 3/2000 | Hoftman | |
| 6,058,933 A | 5/2000 | Good et al. | |
| D428,987 S | 8/2000 | Kwok | |
| 6,112,746 A | 9/2000 | Kwok et al. | |
| 6,123,071 A | 9/2000 | Berthon-Jones et al. | |
| 6,129,082 A | 10/2000 | Leagre | |
| 6,135,109 A | 10/2000 | Blasdell et al. | |
| 6,152,137 A | 11/2000 | Schwartz et al. | |
| D435,650 S | 12/2000 | Kwok | |
| 6,155,986 A | 12/2000 | Brydon et al. | |
| 6,192,886 B1 | 2/2001 | Rudolph | |
| 6,216,691 B1 | 4/2001 | Kenyon et al. | |
| 6,263,874 B1 | 7/2001 | LeDez et al. | |
| 6,342,040 B1 | 1/2002 | Starr et al. | |
| 6,357,441 B1 | 3/2002 | Kwok et al. | |
| 6,397,847 B1 | 6/2002 | Scarberry et al. | |
| 6,401,713 B1 | 6/2002 | Hill et al. | |
| 6,412,487 B1 | 7/2002 | Gunaratnam et al. | |
| 6,412,488 B1 | 7/2002 | Barnett et al. | |
| 6,439,230 B1 | 8/2002 | Gunaratnam et al. | |
| 6,439,231 B1 | 8/2002 | Fukunaga et al. | |
| 6,446,288 B1 | 9/2002 | Pi | |
| 6,459,923 B1 | 10/2002 | Plewes et al. | |
| 6,463,931 B1 | 10/2002 | Kwok et al. | |
| 6,467,483 B1 | 10/2002 | Kopacko et al. | |
| D467,345 S | 12/2002 | Gingles et al. | |
| 6,513,526 B2 | 2/2003 | Kwok et al. | |
| 6,520,182 B1 | 2/2003 | Gunaratnam et al. | |
| 6,581,602 B2 | 6/2003 | Kwok | |
| 6,584,977 B1 | 7/2003 | Serowski | |
| 6,612,306 B1 | 9/2003 | Mault | |
| 6,615,835 B1 | 9/2003 | Cise | |
| 6,626,178 B2 | 9/2003 | Morgan et al. | |
| 6,645,835 B1 | 9/2003 | Cise | |

(56) References Cited

U.S. PATENT DOCUMENTS

| | | |
|---|---|---|
| 6,631,713 B1 | 10/2003 | Christopher |
| 6,631,718 B1 | 10/2003 | Lovell |
| 6,634,358 B2 | 10/2003 | Kwok et al. |
| 6,651,663 B2 | 11/2003 | Barnett et al. |
| 6,694,973 B1 | 2/2004 | Dunhao et al. |
| 6,701,927 B2 | 3/2004 | Kwok et al. |
| 6,729,333 B2 | 5/2004 | Barnett et al. |
| 6,736,139 B1 | 5/2004 | Wix |
| D493,523 S | 7/2004 | Barnett et al. |
| 6,779,524 B2 | 8/2004 | Strawder et al. |
| 6,792,943 B2 | 9/2004 | Kumar et al. |
| 6,796,308 B2 | 9/2004 | Gunaratnam et al. |
| 6,805,117 B1 | 10/2004 | Ho et al. |
| 6,832,610 B2 | 12/2004 | Gradon et al. |
| 6,863,071 B2 | 3/2005 | Annett et al. |
| 6,871,649 B2 | 3/2005 | Kwok et al. |
| 6,892,729 B2 | 5/2005 | Smith et al. |
| 6,895,965 B2 | 5/2005 | Scarberry et al. |
| 6,931,664 B1 | 8/2005 | Chen |
| 6,935,337 B2 | 8/2005 | Virr et al. |
| 6,981,503 B1 | 1/2006 | Shapiro |
| 7,004,168 B2 | 2/2006 | Mace et al. |
| 7,007,696 B2 | 3/2006 | Palkon et al. |
| 7,013,896 B2 | 3/2006 | Schmidt |
| 7,017,576 B2 | 3/2006 | Olsen et al. |
| 7,021,311 B2 | 4/2006 | Gunaratnam et al. |
| 7,028,981 B2 | 4/2006 | Horton |
| 7,036,508 B2 | 5/2006 | Kwok |
| 7,047,971 B2 | 5/2006 | Ho et al. |
| 7,066,179 B2 | 6/2006 | Eaton et al. |
| 7,069,932 B2 | 7/2006 | Eaton et al. |
| 7,069,933 B2 | 7/2006 | Kwok et al. |
| 7,114,498 B1 | 10/2006 | Nashed |
| 7,159,587 B2 | 1/2007 | Drew et al. |
| 7,178,524 B2 | 2/2007 | Noble |
| 7,178,527 B2 | 2/2007 | Kwok et al. |
| 7,210,481 B1 | 5/2007 | Lovell et al. |
| 7,219,669 B1 | 5/2007 | Lovell et al. |
| 7,237,551 B2 | 7/2007 | Ho et al. |
| 7,243,651 B2 | 7/2007 | Kwok et al. |
| 7,287,528 B2 | 10/2007 | Ho et al. |
| 7,341,060 B2 | 3/2008 | Ging et al. |
| 7,383,839 B2 | 6/2008 | Porat et al. |
| 7,445,602 B2 | 11/2008 | Yamamori |
| 7,448,386 B2 | 11/2008 | Ho et al. |
| 7,467,431 B2 | 12/2008 | Weedling et al. |
| 7,487,772 B2 | 2/2009 | Ging et al. |
| 7,487,777 B2 | 2/2009 | Gunaratnam et al. |
| 7,500,280 B2 | 3/2009 | Dixon et al. |
| 7,500,482 B2 | 3/2009 | Biederman |
| 7,614,398 B2 | 11/2009 | Virr et al. |
| 7,631,644 B2 | 12/2009 | Ho et al. |
| 7,665,464 B2 | 2/2010 | Kopacko et al. |
| 7,669,599 B2 | 3/2010 | Gunaratnam et al. |
| 7,700,129 B2 | 4/2010 | Ito et al. |
| 7,743,767 B2 | 6/2010 | Ging et al. |
| 7,753,051 B2 | 7/2010 | Burrow et al. |
| 7,779,832 B1 | 8/2010 | Ho |
| 7,841,988 B2 | 11/2010 | Yamamori |
| 7,870,859 B2 | 1/2011 | Barnett et al. |
| 7,874,292 B2 | 1/2011 | Smith et al. |
| 7,913,337 B1 | 3/2011 | Masson |
| 7,926,487 B2 | 4/2011 | Drew et al. |
| 7,927,285 B2 | 4/2011 | Yamamori |
| 7,931,024 B2 | 4/2011 | Ho et al. |
| 7,938,117 B2 | 5/2011 | Chiesa et al. |
| 7,950,392 B2 | 5/2011 | Kwok et al. |
| 7,975,694 B2 | 7/2011 | Ho |
| 7,997,267 B2 | 8/2011 | Ging et al. |
| 8,001,968 B2 | 8/2011 | Doty et al. |
| 8,001,970 B2 | 8/2011 | King et al. |
| 8,028,699 B2 | 10/2011 | Ho et al. |
| 8,042,539 B2 | 10/2011 | Chandran et al. |
| 8,042,541 B2 | 10/2011 | Amarasinghe et al. |
| 8,056,561 B2 | 11/2011 | Kwok et al. |
| 8,132,270 B2 | 3/2012 | Lang et al. |
| 8,161,971 B2 | 4/2012 | Jaffe |
| 8,191,553 B2 | 6/2012 | Haworth et al. |
| 8,210,181 B2 | 7/2012 | Gunaratnam et al. |
| 8,261,745 B2 | 9/2012 | Chandran et al. |
| 8,261,746 B2 | 9/2012 | Lynch et al. |
| 8,267,091 B2 | 9/2012 | Smith et al. |
| 8,302,224 B2 | 11/2012 | Lehman |
| 8,312,883 B2 | 11/2012 | Gunaratnam et al. |
| 8,336,142 B1 | 12/2012 | See et al. |
| 8,336,549 B2 | 12/2012 | Nashed |
| 8,347,889 B2 | 1/2013 | Farnum |
| 8,365,734 B1 | 2/2013 | Lehman |
| 8,397,724 B2 | 3/2013 | Sher et al. |
| D681,383 S | 5/2013 | Derman et al. |
| 8,443,807 B2 | 5/2013 | McAuley et al. |
| 8,485,190 B2 | 7/2013 | Barnett et al. |
| 8,485,192 B2 | 7/2013 | Davidson et al. |
| 8,490,623 B2 | 7/2013 | Berthon-Jones et al. |
| RE44,453 E | 8/2013 | Virr et al. |
| 8,479,726 B2 | 9/2013 | McAuley |
| 8,522,783 B2 | 9/2013 | Kwok et al. |
| 8,528,558 B2 | 9/2013 | Drew et al. |
| 8,550,081 B2 | 10/2013 | Davidson et al. |
| 8,550,082 B2 | 10/2013 | Davidson et al. |
| 8,550,083 B2 | 10/2013 | Davidson et al. |
| 8,555,885 B2 | 10/2013 | Davidson et al. |
| 8,567,402 B2 | 10/2013 | Gunaratnam et al. |
| 8,567,404 B2 | 10/2013 | Davidson et al. |
| D693,603 S | 11/2013 | Esquivel et al. |
| 8,573,211 B2 | 11/2013 | Ho et al. |
| 8,573,212 B2 | 11/2013 | Lynch et al. |
| 8,573,213 B2 | 11/2013 | Davidson et al. |
| 8,573,214 B2 | 11/2013 | Davidson et al. |
| 8,573,215 B2 | 11/2013 | Davidson et al. |
| 8,573,217 B2 | 11/2013 | Todd et al. |
| 8,578,935 B2 | 11/2013 | Davidson et al. |
| 8,578,939 B1 | 11/2013 | Kimani Mwangi et al. |
| 8,613,280 B2 | 12/2013 | Davidson et al. |
| 8,613,281 B2 | 12/2013 | Davidson et al. |
| 8,616,211 B2 | 12/2013 | Davidson et al. |
| 8,631,792 B2 | 1/2014 | Ho et al. |
| 8,636,006 B2 | 1/2014 | Kwok et al. |
| 8,667,965 B2 | 3/2014 | Gunaratnam et al. |
| 8,684,004 B2 | 4/2014 | Eifler |
| 8,689,366 B2 | 4/2014 | Ho |
| 8,707,950 B1 | 4/2014 | Rubin |
| 8,714,157 B2 | 5/2014 | McAuley et al. |
| 8,752,551 B2 | 6/2014 | Chandran et al. |
| 8,807,134 B2 | 8/2014 | Ho et al. |
| 8,807,135 B2 | 8/2014 | Worboys et al. |
| 8,813,748 B2 | 8/2014 | Kwok et al. |
| 8,881,728 B2 | 11/2014 | Sher et al. |
| 8,915,861 B2 | 12/2014 | Yamamori et al. |
| 8,939,151 B2 | 1/2015 | McAuley et al. |
| 8,944,061 B2 | 2/2015 | D'Souza et al. |
| D726,303 S | 4/2015 | Rollins |
| 9,010,330 B2 | 4/2015 | Barlow et al. |
| 9,010,331 B2 | 4/2015 | Lang et al. |
| 9,022,029 B2 | 5/2015 | Varga et al. |
| 9,027,556 B2 | 5/2015 | Ng et al. |
| 9,138,169 B2 | 9/2015 | Beard |
| 9,186,474 B1 | 11/2015 | Rollins |
| 9,295,799 B2 | 3/2016 | McAuley et al. |
| 9,295,800 B2 | 3/2016 | Davidson et al. |
| D753,287 S | 4/2016 | Darab |
| D753,816 S | 4/2016 | Beard |
| 9,375,545 B2 | 6/2016 | Darkin et al. |
| 9,629,975 B1 * | 4/2017 | Pedro .................... A61M 16/06 |
| 9,981,104 B1 | 5/2018 | Groll |
| 11,298,492 B2 * | 4/2022 | Pedro .................... A61M 16/208 |
| 11,331,446 B2 * | 5/2022 | Pedro .................... A61B 5/082 |
| 11,813,402 B2 * | 11/2023 | Pedro .................... A61M 16/06 |
| 2001/0031929 A1 | 10/2001 | O'Toole |
| 2002/0017300 A1 | 2/2002 | Hickle et al. |
| 2002/0074001 A1 | 6/2002 | Kwok et al. |
| 2002/0174868 A1 | 11/2002 | Kwok et al. |
| 2003/0024533 A1 | 2/2003 | Sniadach |
| 2003/0145859 A1 | 8/2003 | Bohn et al. |

(56) References Cited

U.S. PATENT DOCUMENTS

| | | |
|---|---|---|
| 2003/0183232 A1 | 10/2003 | Fukunaga et al. |
| 2004/0069306 A1 | 4/2004 | Moenning |
| 2004/0221850 A1 | 11/2004 | Ging et al. |
| 2005/0028811 A1 | 2/2005 | Nelson et al. |
| 2005/0145247 A1 | 7/2005 | Nashed |
| 2005/0160532 A1 | 7/2005 | Froelich |
| 2005/0193493 A1 | 9/2005 | Gabbay |
| 2006/0032500 A1 | 2/2006 | Ghiron et al. |
| 2006/0042631 A1 | 3/2006 | Martin et al. |
| 2006/0118117 A1 | 6/2006 | Berthon-Jones et al. |
| 2006/0124131 A1 | 6/2006 | Chandran et al. |
| 2006/0168730 A1 | 8/2006 | Menkedick et al. |
| 2006/0174889 A1 | 8/2006 | Noble |
| 2006/0231091 A1 | 10/2006 | Camarillo |
| 2007/0062536 A1 | 3/2007 | McAuley et al. |
| 2007/0113847 A1 | 5/2007 | Acker et al. |
| 2007/0113856 A1 | 5/2007 | Acker et al. |
| 2007/0267017 A1 | 11/2007 | McAuley et al. |
| 2007/0271699 A1 | 11/2007 | Sacchetti |
| 2007/0295335 A1 | 12/2007 | Nashed |
| 2008/0053446 A1 | 3/2008 | Sleeper et al. |
| 2008/0092898 A1 | 4/2008 | Schneider et al. |
| 2008/0110464 A1 | 5/2008 | Davidson et al. |
| 2008/0196715 A1 | 8/2008 | Yamamori |
| 2008/0221470 A1 | 9/2008 | Sather et al. |
| 2008/0230067 A1 | 9/2008 | Kwok et al. |
| 2009/0069646 A1 | 3/2009 | Yamamori et al. |
| 2009/0084385 A1 | 4/2009 | Lang |
| 2009/0095301 A1 | 4/2009 | Hitchcock |
| 2009/0114229 A1 | 5/2009 | Frater et al. |
| 2009/0114230 A1 | 5/2009 | Hernandez et al. |
| 2009/0133696 A1 | 5/2009 | Remmers et al. |
| 2009/0159084 A1 | 6/2009 | Sher et al. |
| 2009/0178680 A1 | 7/2009 | Chang |
| 2009/0250061 A1 | 10/2009 | Marasigan |
| 2009/0260628 A1 | 10/2009 | Flynn |
| 2009/0301472 A1 | 12/2009 | Kim |
| 2009/0320850 A1 | 12/2009 | Wallnewitz et al. |
| 2010/0113955 A1 | 5/2010 | Colman et al. |
| 2010/0122701 A1 | 5/2010 | Gunaratnam et al. |
| 2010/0122705 A1 | 5/2010 | Moenning, Jr. |
| 2010/0147313 A1 | 6/2010 | Albrecht |
| 2010/0170513 A1 | 7/2010 | Bowditch |
| 2010/0170516 A1 | 7/2010 | Grane |
| 2010/0218316 A1 | 9/2010 | Nissen et al. |
| 2010/0224199 A1 | 9/2010 | Smith et al. |
| 2010/0275919 A1 | 11/2010 | Sung |
| 2010/0313891 A1 | 12/2010 | Veliss et al. |
| 2011/0054366 A1 | 3/2011 | Smith et al. |
| 2011/0072582 A1 | 3/2011 | Patterson et al. |
| 2011/0083670 A1 | 4/2011 | Walacavage |
| 2011/0092930 A1 | 4/2011 | Poorman |
| 2011/0108035 A1 | 5/2011 | Samaniego |
| 2011/0114099 A1 | 5/2011 | Goldstein |
| 2011/0155136 A1 | 6/2011 | Lee |
| 2011/0173750 A1 | 7/2011 | Lehmann |
| 2011/0186050 A1 | 8/2011 | Daly |
| 2011/0214674 A1 | 9/2011 | Ging et al. |
| 2011/0253150 A1 | 10/2011 | King |
| 2011/0265796 A1 | 11/2011 | Amarasinghe et al. |
| 2011/0290253 A1 | 12/2011 | McAuley et al. |
| 2011/0315143 A1 | 12/2011 | Frater |
| 2012/0080035 A1 | 4/2012 | Guney et al. |
| 2012/0111330 A1 | 5/2012 | Gartner |
| 2012/0144588 A1 | 6/2012 | Heimbrock et al. |
| 2012/0180220 A1 | 7/2012 | Popitz |
| 2012/0222680 A1 | 9/2012 | Eves et al. |
| 2012/0227736 A1 | 9/2012 | Bowsher |
| 2012/0234326 A1 | 9/2012 | Mazzone et al. |
| 2012/0247475 A1 | 10/2012 | Hernandez et al. |
| 2012/0271187 A1 | 10/2012 | McNeill |
| 2012/0285455 A1 | 11/2012 | Varga et al. |
| 2012/0285466 A1 | 11/2012 | Pierro et al. |
| 2012/0305001 A1 | 12/2012 | Tatkov |
| 2013/0014760 A1 | 1/2013 | Matula, Jr. et al. |
| 2013/0019870 A1 | 1/2013 | Collazo et al. |
| 2013/0023729 A1 | 1/2013 | Vazales |
| 2013/0060157 A1 | 3/2013 | Beard |
| 2013/0109992 A1 | 5/2013 | Guyette |
| 2013/0146060 A1 | 6/2013 | Ho et al. |
| 2013/0186413 A1 | 7/2013 | Haines et al. |
| 2013/0190643 A1 | 7/2013 | Brambilla |
| 2013/0192601 A1 | 8/2013 | Reischl et al. |
| 2013/0192602 A1 | 8/2013 | Leibitzki et al. |
| 2013/0199537 A1 | 8/2013 | Formica et al. |
| 2013/0319417 A1 | 12/2013 | Weinman |
| 2014/0018691 A1 | 1/2014 | McNeill |
| 2014/0076311 A1 | 3/2014 | Darab |
| 2014/0083425 A1 | 3/2014 | Moenning, Jr. |
| 2014/0144448 A1 | 5/2014 | Eifler |
| 2014/0158135 A1 | 6/2014 | Shyong |
| 2014/0158136 A1 | 6/2014 | Romagnoli et al. |
| 2014/0215687 A1 | 8/2014 | Andrews |
| 2014/0243600 A1 | 8/2014 | Eisenberger |
| 2014/0245537 A1 | 9/2014 | Allen |
| 2014/0251333 A1 | 9/2014 | Burk |
| 2014/0326246 A1 | 11/2014 | Chodkowski et al. |
| 2014/0352072 A1 | 12/2014 | Holladay |
| 2014/0360504 A1 | 12/2014 | Kwok |
| 2015/0047647 A1 | 2/2015 | Winer |
| 2015/0059759 A1 | 3/2015 | Frater et al. |
| 2015/0144140 A1 | 5/2015 | Eury |
| 2015/0217075 A1* | 8/2015 | Nair .................... A61M 16/06 600/531 |
| 2015/0238716 A1 | 8/2015 | Budhiraja et al. |
| 2015/0250970 A1 | 9/2015 | Bowsher |
| 2015/0250971 A1 | 9/2015 | Bachelder et al. |
| 2015/0273170 A1 | 10/2015 | Bachelder et al. |
| 2015/0273171 A1 | 10/2015 | Sullivan et al. |
| 2015/0335852 A1 | 11/2015 | Miller |
| 2016/0015923 A1 | 1/2016 | Chodkowski et al. |
| 2016/0022944 A1 | 1/2016 | Chodkowski et al. |
| 2016/0038709 A1 | 2/2016 | Beard |
| 2016/0067441 A1 | 3/2016 | Bearne et al. |
| 2016/0184540 A1 | 6/2016 | Kokko |
| 2016/0213281 A1* | 7/2016 | Eckerbom ............. B29C 45/44 |
| 2016/0213871 A1 | 7/2016 | Darab |
| 2016/0279368 A1 | 9/2016 | Isenberg |
| 2018/0078726 A1* | 3/2018 | Barraclough ..... A61M 16/0666 |

FOREIGN PATENT DOCUMENTS

| | | |
|---|---|---|
| CN | 103153378 A | 6/2013 |
| CN | 203416833 U | 2/2014 |
| CN | 205073472 U | 3/2016 |
| DE | 19831022 A1 | 1/2000 |
| DE | 19947722 | 4/2001 |
| EP | 2433666 | 3/2012 |
| EP | 3307367 A1 | 4/2018 |
| GB | 187863 | 11/1922 |
| GB | 2209950 A | 6/1989 |
| GB | 2456136 | 7/2009 |
| JP | S4416955 Y | 7/1969 |
| JP | H294566 U | 7/1990 |
| JP | 2003502117 A | 1/2003 |
| JP | 2004321721 A | 11/2004 |
| JP | 2005318975 A | 11/2005 |
| JP | 2008511399 A | 4/2008 |
| JP | 2009172347 A | 8/2009 |
| JP | 2013538631 A | 10/2013 |
| WO | WO-2010059592 | 5/2010 |
| WO | WO-2012094730 A1 | 7/2012 |
| WO | WO-2012106373 A2 | 8/2012 |
| WO | WO-2013036839 | 3/2013 |
| WO | WO-2013064950 | 5/2013 |
| WO | WO-2013142909 A1 | 10/2013 |
| WO | WO-2014038959 | 3/2014 |
| WO | WO-2014077708 A1 | 5/2014 |
| WO | WO-2014210606 | 12/2014 |
| WO | WO-2015063283 | 5/2015 |
| WO | WO-2015131262 | 9/2015 |
| WO | WO-2015147947 | 10/2015 |
| WO | WO-2015187995 | 12/2015 |
| WO | WO-2016007749 | 1/2016 |

(56) References Cited

FOREIGN PATENT DOCUMENTS

| WO | WO-2016028522 A1 | 2/2016 |
|---|---|---|
| WO | WO-2016097948 | 6/2016 |
| WO | WO-2016118922 A1 | 7/2016 |
| WO | WO-2016201358 A1 | 12/2016 |

OTHER PUBLICATIONS

Australian Certificate of Registration issued in application No. 201512962, dated Aug. 11, 2015, 5 pages.
Australian Examination Report No. 1 for Application No. 2015269351, dated Mar. 8, 2019, 5 pages.
Australian Office Action for Application No. 2017328060, dated Sep. 15, 2021, 4 pages.
Australian Office Action for Application No. 2020201805, dated Aug. 3, 2020, 3 pages.
Ball et al., "Performance comparison of two anaesthetic facemasks", Anaesth Intensive Care, Apr. 2007, vol. 35, Issue 2, 226-9 (abstract only), 2 pages.
Canadian Office Action for Application No. 2951226, dated Jun. 22, 2021, 5 pages.
Canadian Office Action issued in Application No. 162891, dated Apr. 5, 2016, 1 page.
Canadian Office Action issued in Application No. 162891, dated Nov. 10, 2015, 7 pages.
Chinese Notification of Grant for Application No. 201530191921.6, dated Feb. 15, 2016, 12 pages.
Chinese Office Action (w/translation) for Application No. 201480042735.9, dated Apr. 5, 2017, 18 pages.
Chinese Office Action for Application No. 201480042735.9, dated Nov. 6, 2017, 21 pages.
Chinese Office Action for Application No. 201580029981.5, dated Apr. 15, 2019, 12 pages.
Chinese Office Action for Application No. 201580029981.5, dated Oct. 8, 2019, 14 pages.
Chinese Office Action for Application No. 201580029981.5, dated Sep. 5, 2018, 14 pages.
Chinese Office Action for Application No. 201730161613.8, dated Aug. 7, 2017, 2 pages.
Chinese Office Action for Application No. 201730161613.8, dated Sep. 19, 2017, 11 pages.
Chinese Office Action for Application No. 201780070064.0, dated Apr. 8, 2021, 17 pages including translation.
Chinese Office Action for Application No. 201780070064.0, dated Oct. 9, 2021, 18 pages including translation.
CPAP product description, http://www.cpap.com/productpage/pr-amara-full-face-cpap-mask-gel-silicone.html, downloaded Jul. 28, 2016, 11 pages.
CPAPXCHANGE product image, http://www.cpapexchange.com/cpap-masks-bipap-masks/bluegel-full-cushion-comfortgel-cpap-bipap-masks.jpg, downloaded Jul. 28, 2016, 1 page.
DirectHome Medical product description, http://www.directhomemedical.com/profilelite-gel-cpap-mask-philipsrespironics.html#.VwXLIPkrLIU, downloaded Jul. 28, 2016, 6 pages.
English Translation of Japanese Office Action for Application No. 2016-005262, dated Jun. 30, 2016, 1 page.
English Translation of Japanese Office Action for Application No. 2016-005263, dated Jun. 30, 2016, 1 page.
European Office Action for Application No. 003933217-0001, dated May 16, 2017, 2 pages.
European Partial Supplementary European Search Report for Application No. 14818563.0, dated Jan. 30, 2017, 6 pages.
Extended European Search Report for Application No. 14818563.0, dated May 3, 2017, 12 pages.
Extended European Search Report for Application No. 15803670.7, dated Oct. 24, 2018, 12 pages.
Extended European Search Report for Application No. 15833101.7, dated Jul. 3, 2018, 13 pages.
Extended European Search Report for Application No. 17851288.5, dated Apr. 22, 2020, 14 pages.
Extended European Search Report for Application No. 20165643.6, dated Jun. 24, 2020, 7 pages.
Indian Office Action for Indian Design Patent Application No. 272704, dated Aug. 28, 2015, 13 pages.
InnoMed Technologies Sylent Mask product description, http://innomedinc.com/sylent-ne-disposable-nasal-mask/, downloaded Jul. 28, 2016, 2 pages.
InnoMed Technologies, Hybrid Mask product description, http://innomedinc.com/hybrid/, downloaded Jul. 28, 2016, 4 pages.
International Preliminary Report on Patentability for Application No. PCT/US2014/044934, dated Jan. 7, 2016, 12 pages.
International Preliminary Report on Patentability for Application No. PCT/US2015/021323, dated Oct. 6, 2016, 8 pages.
International Preliminary Report on Patentability for Application No. PCT/US2015/044341, dated Mar. 2, 2017, 10 pages.
International Preliminary Report on Patentability for Application No. PCT/US2016/037070, dated Dec. 12, 2017, 7 pages.
International Preliminary Report on Patentability for Application No. PCT/US2015/034277, dated Dec. 15, 2016, 11 pages.
International Search Report and Written Opinion for Application No. PCT/US14/44934, dated Jan. 2, 2015, 16 pages.
International Search Report and Written Opinion for Application No. PCT/US2015/044341, dated Jan. 7, 2016, 13 pages.
International Search Report and Written Opinion for Application No. PCT/US2015/34277, dated Nov. 23, 2015, 16 pages.
International Search Report and Written Opinion for Application No. PCT/US2016/037070, dated Nov. 10, 2016, 11 pages.
International Search Report and Written Opinion for Application No. PCT/US2017/048046, dated Nov. 6, 2017, 11 pages.
Invitation to Pay Additional Fees for Application No. PCT/US14/44934, dated Oct. 24, 2014, 3 pages.
Invitation to Pay Additional Fees for Application No. PCT/US15/44341, dated Oct. 21, 2015, 2 pages.
Israeli Notice of Allowance for Application No. 57056 (w/translation of relevant portions), dated Nov. 1, 2015, 3 pages.
Israeli Notice of Allowance for Application No. 57056 (no translation), dated May 29, 2016, 1 page.
Israeli Office Action for Application No. 57850 (w/translation of relevant portions), dated Feb. 14, 2016, 3 pages.
Israeli Office Action for Application No. 58250 (w/translation of relevant portions), dated Jun. 29, 2016, 2 pages.
Israeli Office Action issued in application No. 58250 (w/translation of relevant portions), dated Jul. 18, 2016, 3 pages.
Japanese Decision for Registration (w/translation) for Application No. 2016-006559, dated May 12, 2017, 2 pages.
Japanese Decision for Registration (w/translation) for Application No. 2016-006560, dated May 12, 2017, 2 pages.
Japanese Decision for Registration for Application No. 2016-005263, dated Dec. 22, 2017, 4 pages.
Japanese Decision for Registration for Application No. 2017-009813, dated Oct. 6, 2017, 2 pages.
Japanese Office Action (w/translation) for Application No. 2016-005262, dated Apr. 28, 2017, 7 pages.
Japanese Office Action (w/translation) for Application No. 2016-005263, dated Apr. 28, 2017, 7 pages.
Japanese Office Action (w/translation) for Application No. 2016-006559, dated Sep. 2, 2016, 3 pages.
Japanese Office Action (w/translation) for Application No. 2016-006560, dated Sep. 2, 2016, 3 pages.
Japanese Office Action for Application No. 2015-013148, dated Dec. 18, 2015, 3 pages.
Japanese Office Action for Application No. 2016-005262, dated Dec. 22, 2017, 4 pages.
Japanese Office Action for Application No. 2016-571111, dated Jun. 11, 2019, 10 pages.
Japanese Office Action for Application No. 2017-009813, dated Jul. 28, 2017, 3 pages.
Japanese Office Action for Application No. 2017-509724, dated Jul. 24, 2018, 12 pages.
Japanese Office Action for Application No. 2019-515265, dated Nov. 24, 2021, 6 pages including translation.

(56) References Cited

OTHER PUBLICATIONS

Japanese Office Action for Application No. 2020098813, dated Jun. 22, 2021, 9 pages including translation.
Korean Design of Registration for Application No. 30-2015-0029561, M002 (w/translation), dated Jul. 27, 2016, 3 pages.
Korean Notice of Design of Registration for Application No. 30-2015-0029561, M001 (w/translation), dated Jun. 29, 2016, 3 pages.
Korean Office Action for Application No. 30-2015-0029561, M0001, dated Jun. 9, 2016, 16 pages.
Korean Office Action for Application No. 30-2015-0029561, M001 (w/translation), dated Dec. 24, 2015, 12 pages.
Korean Office Action for Application No. 30-2015-0029561, M001, dated May 23, 2016, 2 pages.
Korean Office Action for Application No. 30-2015-0029561, M002 (w/translation), dated Dec. 24, 2015, 7 pages.
Korean Office Action for Application No. 30-2015-0029561, M002 (w/translation), dated May 23, 2016, 6 pages.
Liang, Yafen et al., "Nasal Ventilation is More Effective than Combined Oral-Nasal Ventilation during Induction of General Anesthesia in Adult Subjects", Anesthesiology 2008, vol. 108, No. 6, Jun. 2008, pp. 998-1003.
Mexican Office Action for Application No. MX/a/2016/015858, dated Feb. 25, 2021, 9 pages including machine translation.
New Zealand Office Action for Application No. 764985, dated Sep. 20, 2021, 4 pages.
Notice of Allowance (corrected) for U.S. Appl. No. 15/288,973, dated Feb. 10, 2017, 16 pages.
Notice of Allowance (corrected) for U.S. Appl. No. 15/288,973, dated Mar. 10, 2017, 9 pages.
Notice of Allowance (corrected) for U.S. Appl. No. 15/288,973, dated Mar. 24, 2017, 9 pages.
Notice of Allowance for U.S. Appl. No. 15/288,973, dated Feb. 1, 2017, 25 pages.
Notice of Decision of Registration for Design for Korean Design Application No. 30-20016-0014111, dated Dec. 13, 2016, 3 pages.
Office Action for U.S. Appl. No. 29/520,420, dated Aug. 11, 2016, 18 pages.
Office Action for U.S. Appl. No. 29/530,124, dated Aug. 12, 2016, 17 pages.
Office Action for U.S. Appl. No. 15/272,074, dated Apr. 19, 2017, 54 pages.
Office Action for U.S. Appl. No. 15/272,074, dated Jul. 31, 2017, 34 pages.
Office Action for U.S. Appl. No. 15/272,074, dated Sep. 13, 2017, 5 pages.
Office Action for U.S. Appl. No. 15/272,160, dated Apr. 24, 2017, 39 pages.
Office Action for U.S. Appl. No. 15/272,160, dated Dec. 15, 2017, 34 pages.
Office Action for U.S. Appl. No. 15/272,160, dated Jan. 4, 2017, 31 pages.
Office Action for U.S. Appl. No. 15/272,190, dated Dec. 28, 2017, 22 pages.
Office Action for U.S. Appl. No. 15/272,190, dated Jan. 30, 2017, 32 pages.
Office Action for U.S. Appl. No. 15/272,190, dated Jun. 21, 2017, 7 pages.
Office Action for U.S. Appl. No. 15/272,190, dated May 23, 2017, 36 pages.
Office Action for U.S. Appl. No. 15/288,973, dated Dec. 14, 2016, 21 pages.
Office Action for U.S. Appl. No. 29/520,420, dated Apr. 7, 2017, 3 pages.
Office Action for U.S. Appl. No. 29/520,420, dated Dec. 8, 2017, 5 pages.
Office Action for U.S. Appl. No. 29/520,420, dated Feb. 24, 2017, 14 pages.
Office Action for U.S. Appl. No. 29/520,420, dated Jun. 15, 2017, 12 pages.
Office Action for U.S. Appl. No. 29/530,124, dated Apr. 19, 2017, 6 pages.
Office Action for U.S. Appl. No. 29/530,124, dated Aug. 30, 2017, 3 pages.
Office Action for U.S. Appl. No. 29/530,124, dated Aug. 9, 2017, 11 pages.
Office Action for U.S. Appl. No. 29/530,124, dated Feb. 28, 2017, 16 pages.
Office Action for U.S. Appl. No. 29/530,124, dated Jun. 21, 2017, 14 pages.
Office Action for U.S. Appl. No. 29/530,124, dated Nov. 29, 2017, 31 pages.
Partial Supplementary European Search Report for Application No. 16808466.3, dated Jan. 22, 2019, 14 pages.
Singapore Invitation to Respond to Written Opinion for Application No. 11201610048P, dated Sep. 19, 2017, 16 pages.
Singapore Invitation to Respond to Written Opinion for Application No. 11201701253U, dated Nov. 8, 2017, 12 pages.
Singapore Search Report for Application No. 11201510589T, dated Jan. 31, 2017, 11 pages.
Sleep Medicine Solutions product description, Http://sleepmedicinesolutions.net.au/cpap-spare-parts/26-fisher-paykel-zest-foams.html, downloaded Jul. 28, 2016, 2 pages.
Sleepnet homepage, https://web.archive.org/web/20111021122613/http://www.sleepnetmasks.com/, downloaded Jul. 28, 2016, 4 pages.
European Office Action for Application No. 20165643.6, dated Apr. 25, 2022, 3 pages.
Japanese Office Action for Application No. 2022-053950, dated Oct. 21, 2022, 4 pages, including translation.
Australian Office Action for Application No. 2017328060, dated May 10, 2022, 2 pages.
Extended European Search Report for Application No. 21206190.7, dated Mar. 10, 2022, 11 pages.
Official Action for Australia Patent Application No. 2022275401, dated Nov. 21, 2023 3 pages.
Official Action with English Translation for Brazil Patent Application No. BR112019004967-3, dated Mar. 2, 2023 5 pages.
Official Action for Canada Patent Application No. 3,036,797, dated Aug. 7, 2023 3 pages.
Intention to Grant for European Patent Application No. 21206190.7, dated Oct. 17, 2023 35 pages.
Decision to Grant with Machine Translation for Japan Patent Application No. 2023-029793, dated Aug. 29, 2023 2 pages.
Official Action for U.S. Appl. No. 16/333,215, dated May 20, 2021 24 pages.
Notice of Allowance for U.S. Appl. No. 16/333,215, dated Sep. 13, 2021 9 pages.
Intention to Grant for European Patent Application No. 21206190.7, dated Mar. 6, 2024 35 pages.

\* cited by examiner

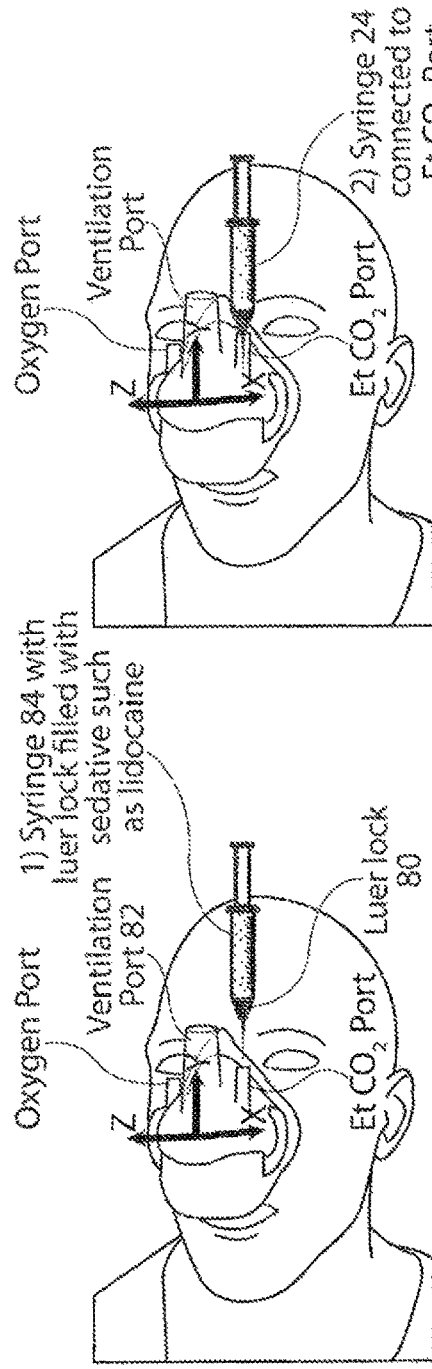
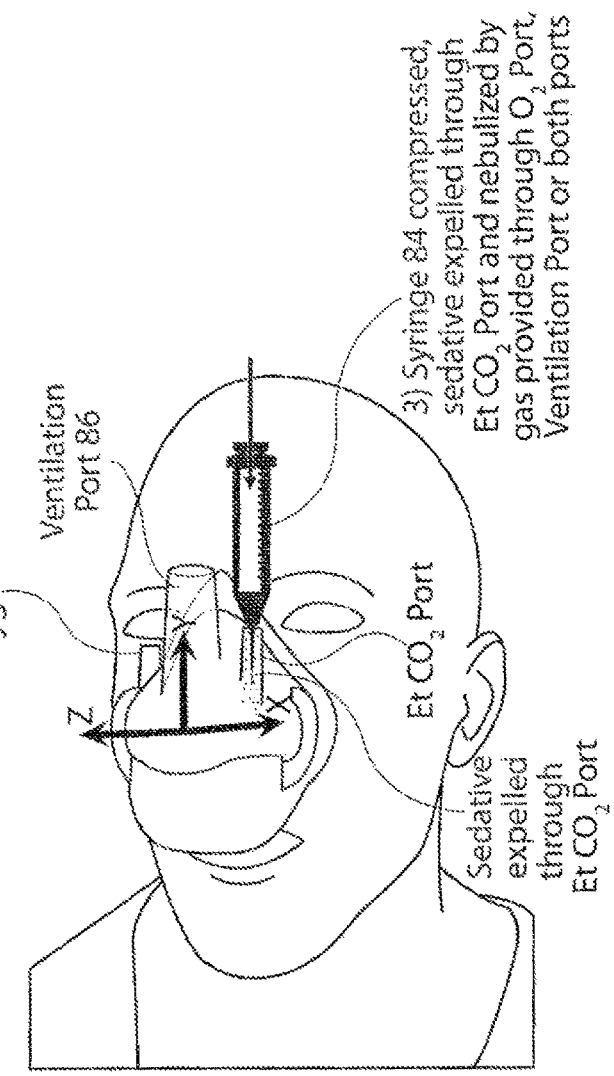
FIG. 8A
FIG. 8B
FIG. 8C

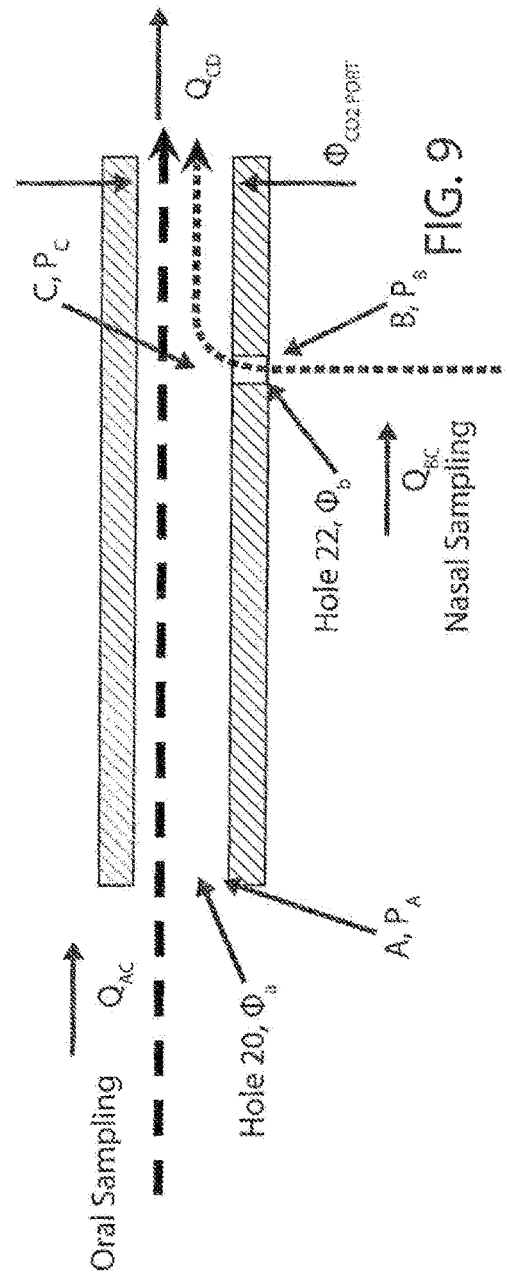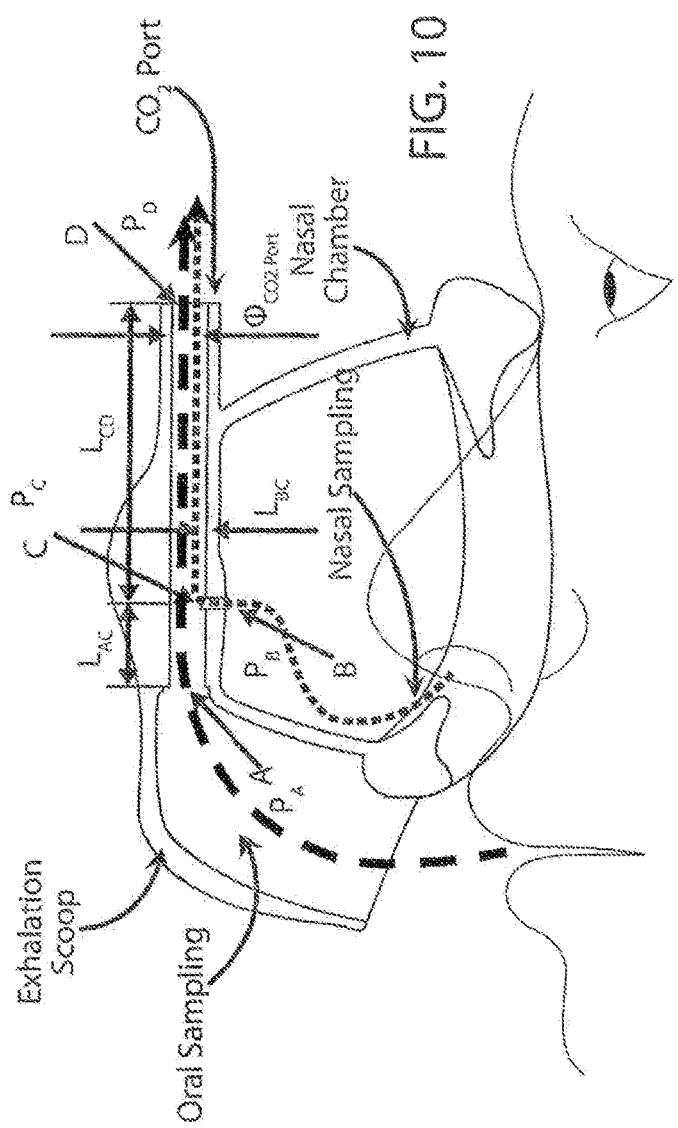

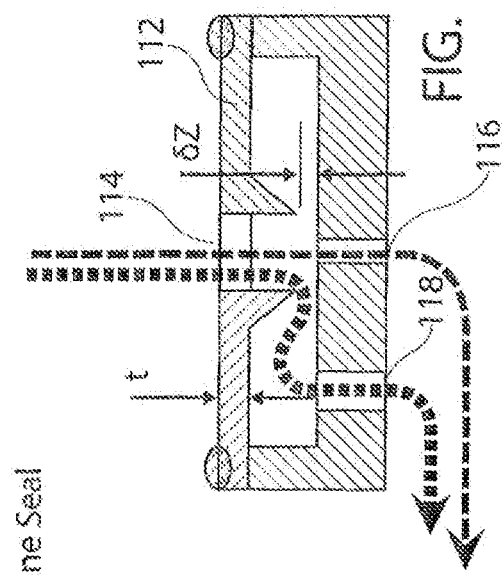
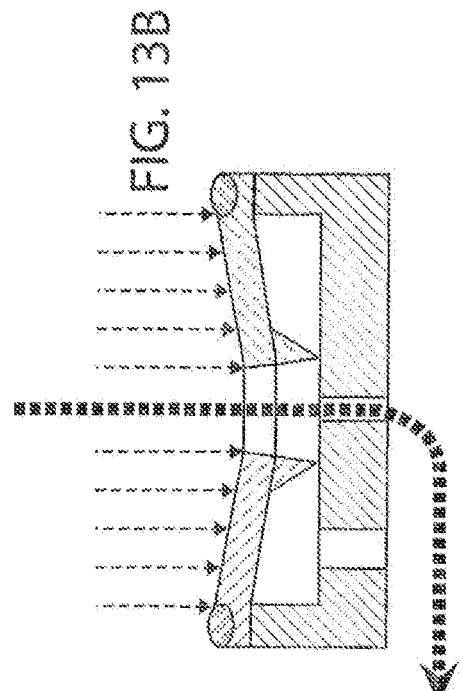
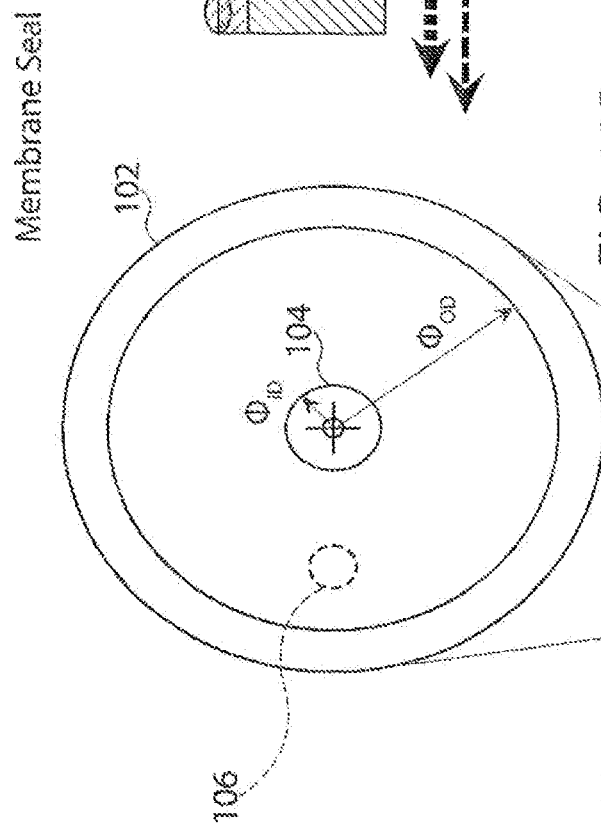
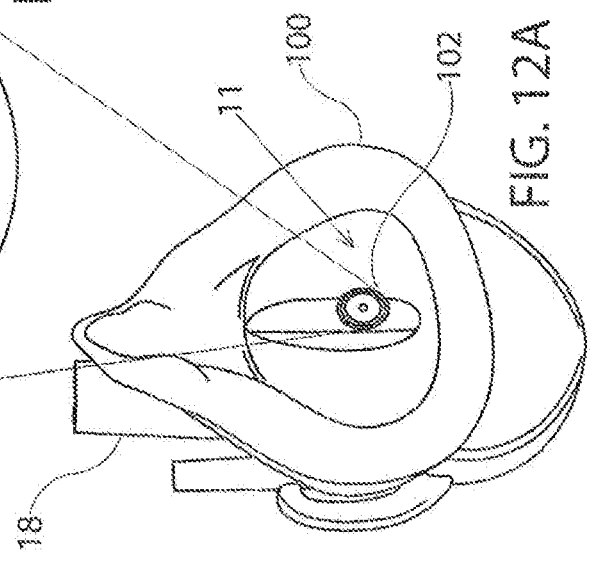
FIG. 12A
FIG. 12B
FIG. 13A
FIG. 13B

Figure 12C- Sectional View of Et Seal

VENTILATION MASK

CROSS-REFERENCE TO RELATED APPLICATIONS

This application is a continuation of U.S. patent application Ser. No. 16/333,215 filed Mar. 13, 2019, which issued as U.S. Pat. No. 11,298,492 on Apr. 12, 2022, which claims priority from PCT Patent Application Serial No. PCT/2017/048046, filed Aug. 22, 2017, which claims priority from U.S. Provisional Application Ser. No. 62/510,192, filed May 23, 2017, and from U.S. Provisional Application Ser. No. 62/467,808, filed Mar. 6, 2017 and from U.S. Provisional Application Ser. No. 62/425,371, filed Nov. 22, 2016 and from U.S. Provisional Application Ser. No. 62/394,405, filed Sep. 14, 2016, the disclosure of each of which is incorporated herein by reference in its entirety.

BACKGROUND OF THE INVENTION

The present invention relates to improvements in anesthesia masks and ventilation masks.

During surgery a patient usually is placed under anesthesia. The most common delivery system consists of canisters containing anesthesia gases and oxygen, a system of regulating the gas flow and the patient's breathing, and a device ensuring the potency of the patient's airway for breathing, oxygenation and the delivery of the anesthetic gas mixture. A ventilation mask is used to provide oxygen to the patient either during emergency and/or elective airway management, which includes but is not limited to: before a patient is anesthetized for surgery; while the patient is sedated during the surgery or procedure; while the patient is recovering from anesthesia; after the patient has recovered from anesthesia; and during any event where a patient requires supplemental oxygen. However, conventional ventilation masks are less than ideal.

Moreover, situations may arise during surgery that require rapid intubation of a patient. Full face masks, i.e. masks covering both the nose and mouth of a patient are problematic in emergency situations since a mask must be removed to uncover the mouth of a patient for intubation. However, removing the mask also removes oxygen support.

In our co-pending PCT Application Serial Nos. PCT/US2014/44934, PCT/US2015/034277 and PCT/US2015/044341 (hereinafter the '934, '277 and '341 PCT applications), we provide improved ventilation/anesthesia masks that overcome the aforesaid and other problems with the prior art by providing, in one aspect, a combination mask comprising a nasal portion or mask and an oral portion or mask defining respectively a nasal chamber and an oral chamber, detachably connected to one another wherein the nasal mask may be used separately or connected to the oral mask as a combination nasal/oral mask. We also provide a nasal mask with one or more ports, and various strap systems for holding the mask on a patient's face. We also provide a nasal only mask with one or more sensors for sensing end-tidal $CO_2$ or other gases, and for scavenging gases. See our co-pending PCT Application Serial No. PCT/US16/037070 (hereafter the '070 PCT application). Such combination nasal/oral masks and nasal only masks are available commercially from Revolutionary Medical Devices, Inc. of Tucson, Arizona, under the trademark SuperNO$_2$VA®.

The present invention provides improvements in nasal masks such as described in our aforesaid PCT applications, by providing an exhalation scoop adjacent the bottom of the nasal mask to overlay at least in part the upper lip of a patient, when the mask is worn. The exhalation scoop may be formed of a flexible, preferably resiliently deformable material, and fixed mechanically or adhesively to the mask. Alternatively, the exhalation scoop may be formed with a lip to fit in a matching groove in the outer surface of the nasal mask, or formed integrally with the mask. The exhalation scoop is flexible so as to permit a surgeon to compress or push the exhalation scoop out of the way to permit access to the patient's mouth, while the nasal mask remains on the patient. Alternatively, the exhalation scoop may be folded back on itself leaving access to the patient's mouth, while the nasal mask remains on the patient.

In one aspect the invention provides a nasal mask having exhalation scoop formed of a the flexible or resiliently deformable material, fixed adjacent a lower portion of mask, adapted to overlie an upper lip of a patient when the mask is worn.

In another aspect the exhalation scoop is adapted to be pressed out of the way to permit access to the mouth of a patient.

In still another aspect the exhalation scoop is adapted to be folded back on itself to permit access to the mouth of a patient.

In yet another aspect, the mask includes an end-tidal $CO_2$ port for sampling exhaled $CO_2$ expelled from a mouth and/or nose of a patient.

In still yet another aspect the mask includes a ventilation port adapted to attach to an anesthesia machine, ventilation machine, hyperinflation bag or other ventilation or gas accessory.

In a still further aspect the mask further includes an oxygen port adapted for connection to an oxygen source for supplying oxygen to an interior of the mask.

In another aspect, the mask has tabs or eyelets for attaching one or more mask straps.

The present invention also provides a method for ventilating a patient, comprising providing a nasal mask having exhalation scoop formed of a the flexible or resiliently deformable material, fixed adjacent a lower portion of mask, and adapted to overlie an upper lip of a patient when the mask is worn, and when needed, moving the exhalation scoop out of the way to provide access to the patient's mouth.

In one aspect of the method the exhalation scoop is pressed out of the way to permit access to the mouth of a patient.

In another aspect of the method the exhalation scoop is folded back on itself to permit access to the mouth of a patient.

In still yet another aspect the method includes providing a nasal mask with a exhalation scoop as described above, and monitoring end-tidal $CO_2$ port by sampling exhaled $CO_2$ expelled from a mouth and/or nose of a patient using an end-tidal $CO_2$ monitor.

In still yet another aspect, the mask is attached to an anesthesia machine, ventilation machine, hyperinflation bag or other ventilation or gas accessory, or to an oxygen source for supplying oxygen to an interior of the mask.

The present invention also provides a nasal mask having an exhalation scoop fixed adjacent a lower portion of the mask, adapted to overly an upper lip of a patient when the mask is worn, wherein said exhalation scoop includes an opening permitting access to a mouth of a patient when the mask is worn, and a flexible flap arranged on an inside surface of the scoop for closing off the opening. In one embodiment, the opening comprises an aperture or one or more slits.

The invention also provides a method for ventilating a patient, comprising providing a nasal mask having an exhalation scoop fixed adjacent a lower portion of the mask and adapted to overly at least in part the mouth of the patient when a mask is worn, wherein the exhalation scoop includes an aperture permitting access to the mouth of the patient, and accessing the mouth of the patient by pushing a functional tool through the aperture.

In one embodiment, the tool is removed, the aperture is essentially closed by the flap.

Also provided is a nasal mask having an exhalation scoop fixed adjacent a lower portion of the mask, adapted to overly the mouth of a patient, at least in part, when the mask is worn, said mask further including an end-tidal $CO_2$ port for sampling exhaled $CO_2$ expelled from a mouth and nose of the patient, wherein said end-tidal $CO_2$ port is further provided with an interface for connecting with an interface connector.

In one embodiment, the interface connector comprises a luer lock interface connector. Finally, the invention provides a method for ventilating a patient, comprising providing a nasal mask as above described, and introducing a fluid into the interior of the mask through the interface connector.

In one embodiment, the fluid comprises a sedative such as lidocaine.

In another embodiment, the fluid added through the interface connector is mixed with gases within the mask.

In yet another embodiment, the present invention provides improvements over the nasal mask as described above, and having oral and nasal $CO_2$ sampling ports, by providing a mechanism for substantially balancing flow between the oral and nasal $CO_2$ sampling ports of the mask.

More particularly, the present invention provides a pressure-based flow resistor located inside the nasal chamber of the mask for maintaining substantially constant flow between the nasal and oral sampling openings by varying resistance as a function of differential pressure between the nasal and oral chambers.

In one aspect of the invention there is provided a nasal mask having an exhalation scoop fixed adjacent a lower portion of mask, adapted to overlie an upper lip of a patient when the mask is worn, said mask including first port for sampling exhaled $CO_2$ expelled from a mouth of the patient, and a second port for sampling exhaled $CO_2$ expelled from a nose of a patient, said mask further including a pressure-based flow resistor communicating with said second post adapted to maintain substantially constant sampling flow of $CO_2$ expelled from the mouth and nose of the patient to the end-tidal $CO_2$ port.

In still another embodiment the pressure-based flow resistor maintains constant flow by maintaining constant flow by varying resistance as a function of differential pressure, between the first port and the second port, $Q_{BC}$, as defined by $(PB-PC)^{1/2}/R_{BC}$.

In another aspect, the pressure-based flow resistor comprises a manifold having two or more holes which communicated between a nasal chamber of the mask and an end tidal $CO_2$ port, and flow occurs due to differential pressure between the nasal chamber and the end-tidal $CO_2$ port.

In yet another aspect the manifold comprises a flexible membrane that deflects as a function of pressure and varies the flow resistance to the end tidal $CO_2$ port. In such aspect the deflection amount, $\delta Z$, preferably varies with resistance $R_{BC}$, in proportion to the differential pressure $P_B-P_C$.

In another aspect the maximum flow resistance is defined by a geometry of a hole in the membrane that is not blocked by the membrane due to a central opening n the membrane.

In still another aspect the membrane blocks flow to one or more holes in the membrane when pressure deflects the membrane in the Z direction.

The present invention also provides a method for ventilating a patient, comprising providing a nasal mask having an exhalation scoop fixed adjacent a lower portion of mask, adapted to overlie an upper lip of a patient when the mask is worn, said mask including first port for sampling exhaled $CO_2$ expelled from a mouth of the patient, and a second port for sampling exhaled $CO_2$ expelled from a nose of a patient, said mask further including a pressure-based flow resistor communicating with said second post adapted to maintain substantially constant sampling flow of $CO_2$ expelled from the mouth and nose of the patient to the end-tidal $CO_2$ port, and connecting the sampling flow to an end-tidal $CO_2$ port.

In another aspect of the method the pressure-based flow resistor maintains constant flow by maintaining constant flow by varying resistance as a function of differential pressure, between the first port and the second port, $Q_{BC}$, as defined by $(PB-PC)^{1/2}/R_{BC}$.

In still yet another aspect of the method the pressure-based flow resistor comprises a manifold having two or more holes which communicate between a nasal chamber of the mask and an end tidal $CO_2$ port, and flow occurs due to differential pressure between the nasal chamber and the end-tidal $CO_2$ port.

In yet another aspect of the method the manifold comprises a flexible membrane that deflects as a function of pressure and varies the flow resistance to the end tidal $CO_2$ port. In such aspect the deflection amount, $\delta Z$, preferably varies with resistance $R_{BC}$, in proportion to the differential pressure $P_B-P_C$.

In still yet another aspect of the method the maximum flow resistance is defined by a geometry of a hole in the membrane that is not blocked by the membrane due to a central opening n the membrane.

In yet another aspect of the method the membrane blocks flow to one or more holes in the membrane when pressure deflects the membrane in the Z direction.

Further features and advantages of the present invention will be seen from the following detailed description, taken in conjunction with the accompanying, wherein FIGS. 1A-1D are front, rear, top and perspective views respectively, of a nasal mask incorporating an exhalation scoop in accordance with a first embodiment of the present invention;

FIGS. 8A, 8B and 8C are perspective views similar to FIG. 2 of yet another and fourth embodiment of the invention;

FIG. 9 is a side elevational view, in cross section, of the $CO_2$ sampling port of the FIG. 2 mask;

FIG. 10 is a side elevational view, in cross section, of the mask in FIG. 2;

FIG. 12A is a perspective view, from the inside, of a mask in accordance with a preferred embodiment of the present invention;

FIG. 12B is an enlarged view of a flexible seal flap valve of the nasal mask of FIG. 12A;

FIG. 13A is a side elevational view, in cross section, of the seal of FIG. 12B in an open position; and FIG. 13B is a view, similar to FIG. 13A, of the seal flap valve of FIG. 13A.

As used herein "nasal mask" preferably comprises a nasal mask similar to the nasal mask such as described in our aforesaid '934, '277, '341, and '070 PCT Applications including in particular a SuperNO$_2$VA® nasal mask available commercially from Revolutionary Medical Devices, Inc. of Tucson, Arizona.

FIGS. 1A-1D are front, rear, top and perspective views of a nasal mask 10 somewhat similar to the nasal mask described in FIGS. 16A-16E our aforesaid PCT Application No. PCT/US16/37070, but having an exhalation scoop 12 formed of a flexible, preferably resiliently deformable material, fixed to a lower portion 14 of the mask. Exhalation scoop 12 preferably has a 00 Durometer Hardness of 0020 to 0050, to a Shore A Hardness of 2-10, more preferably a Shore A Hardness of 3-7, most preferably a Shore A Hardness of about 5. The softer the material the better.

Figure 1:
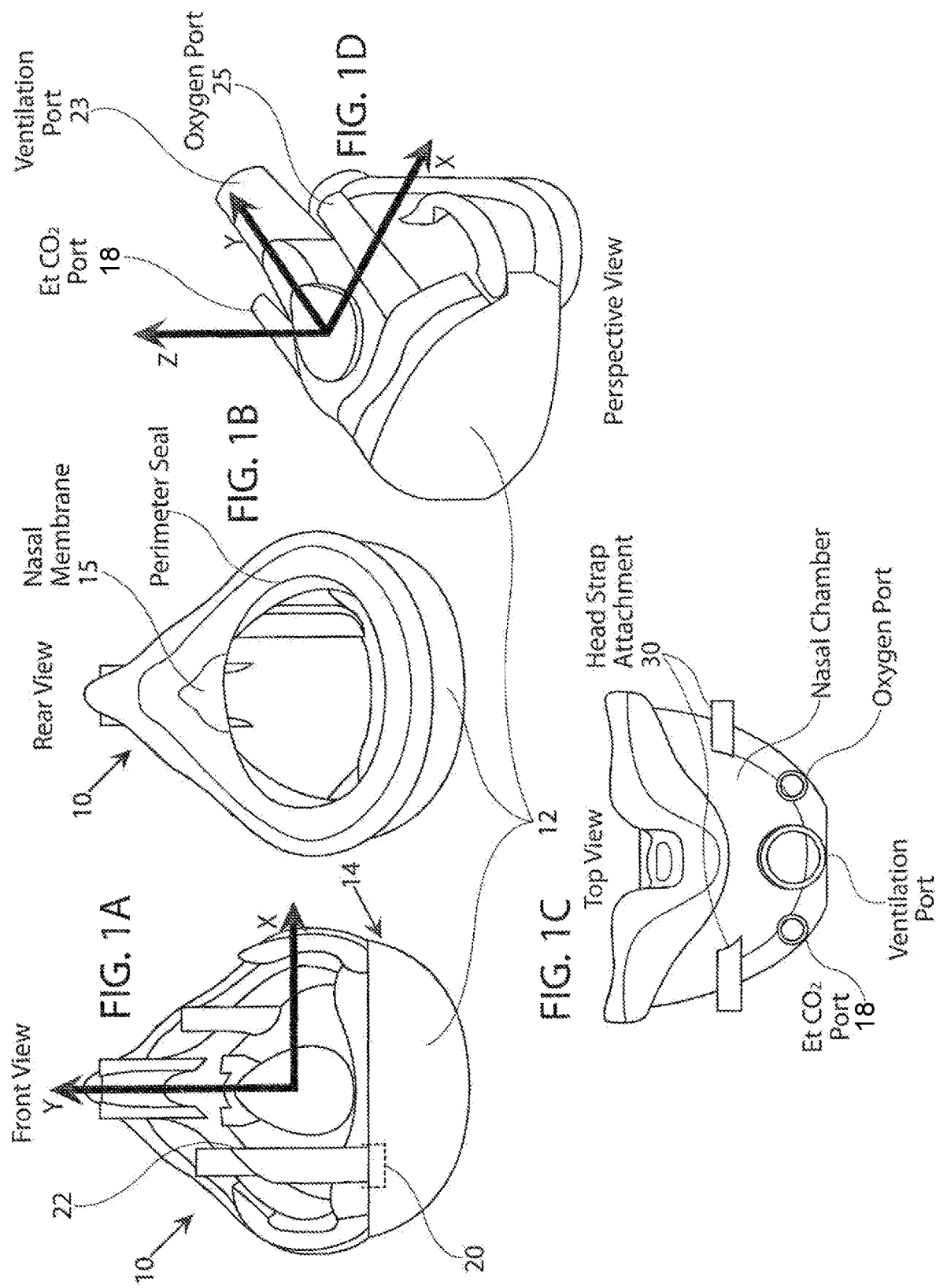
Figure 2:
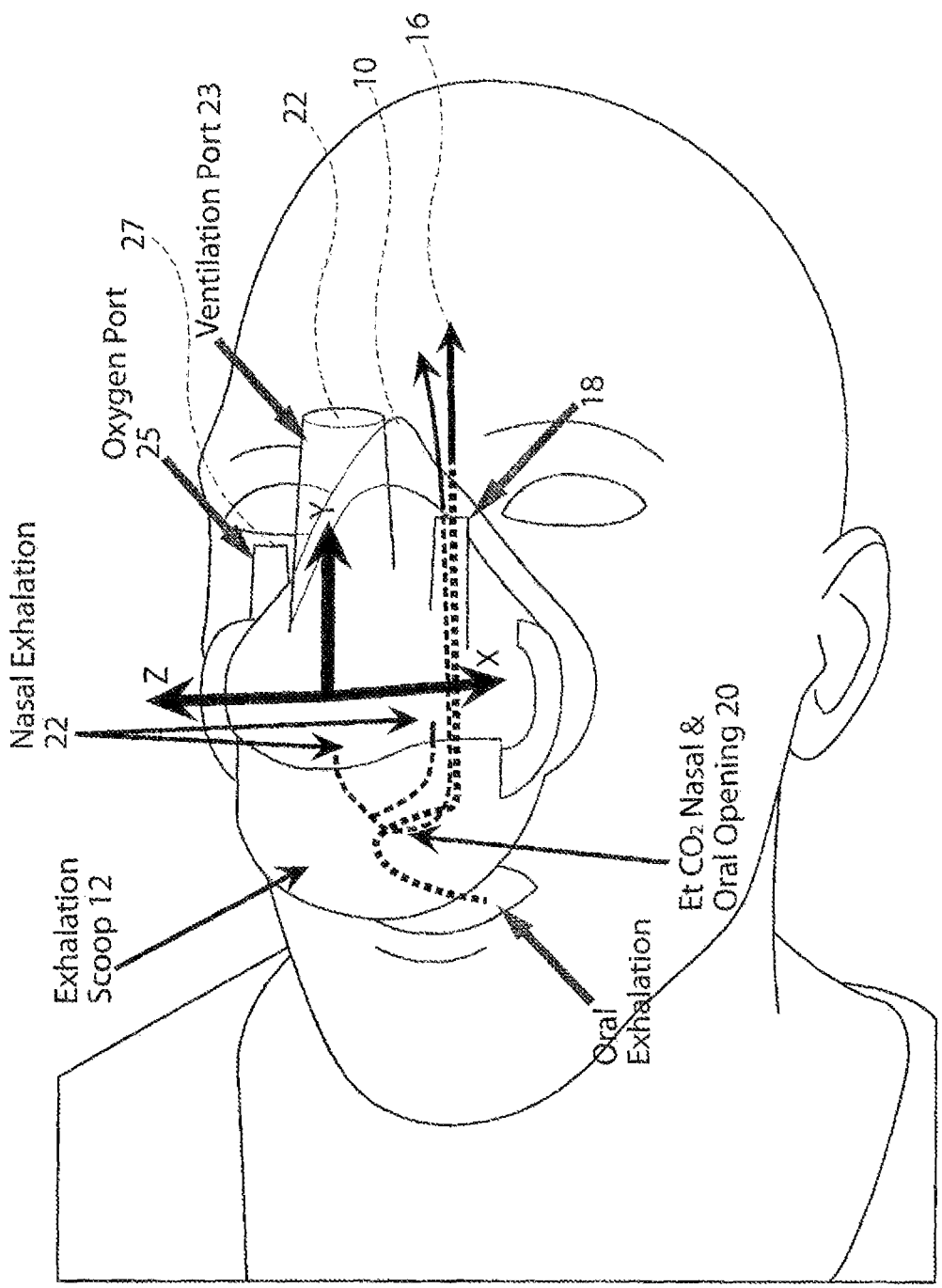
FIG. 2 is a perspective view showing nasal mask with an exhalation scoop in accordance with the present invention on a patient.

Referring also to FIG. 2, the mask 10 also includes a gas sampling device (shown in phantom at 16) adapted for suction attached to an end-tidal ("ET") $CO_2$ port 18 and adapted for drawing gas samples from both the oral and nasal exhalations of the patient. One opening 20 of the EtCO$_2$ manifold is located behind the exhalation scoop 12 to overlie the upper lip of a patient, when the mask is worn by a patient, on the exterior of the nasal mask 10, where a negative pressure (pressure less than atmospheric pressure) is created by a gas sampling device 16. A second opening 22 of the manifold is located to underlie the nares of the patient, on the interior of the nasal mask where a negative pressure is also created by the gas sampling device 16. When the patient exhales, oral and nasal exhalation are collected through openings 20, 22 and proceed through the manifold and exit the EtCO$_2$ port that is connected to the gas sampling device 16 that provided the negative pressure. Concentration levels of the gas, such as $CO_2$ are then measured by gas sampling device 16.

The nasal mask interior chamber is pressurized through a ventilation port 23 by an anesthesia machine or another ventilation device (shown in phantom at 24). Flow from the patient's nose is drawn to the negative pressure of the opening of the manifold interior of the nasal chamber. The patient's mouth is at atmospheric pressure and the flow of the oral exhalation is channeled by the exhalation scoop where it is drawn by the negative pressure presented by gas sampling system through the manifold opening. Samples of both the nasal and oral exhalation flow through a manifold, and exit the EtCO$_2$ port 18 to the gas sampling device 16.

The mask 10 also includes an oxygen port 25 for supplying oxygen from an oxygen source (shown in phantom at 27) to a patient.

Figure 3:
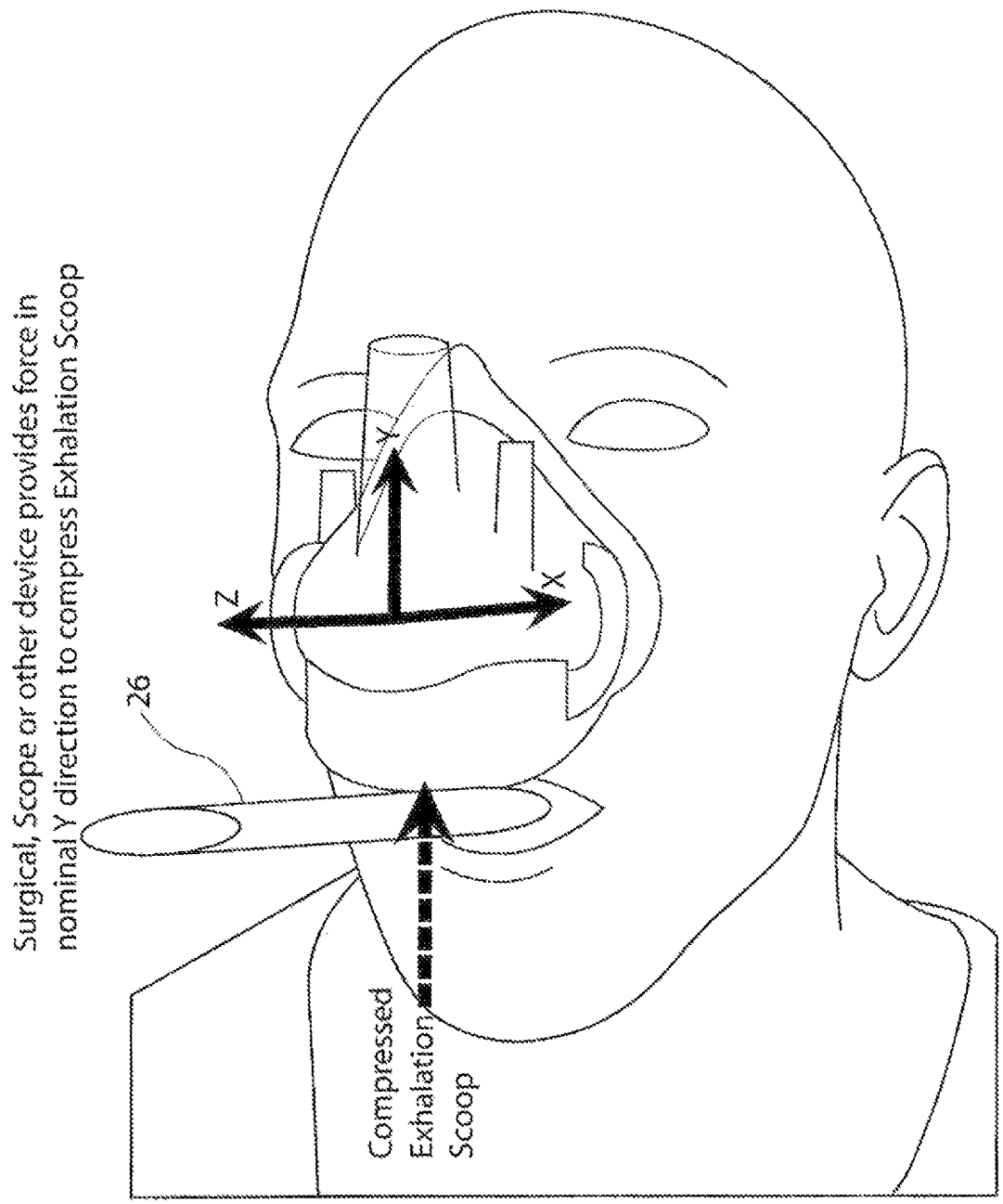
FIG. 3 is a view similar to FIG. 2, showing the exhalation scoop compressed or pushed out of the way to provide oral access.

One benefit of the flexible exhalation scoop design is that if the surgeon requires access to the patients mouth to employ a device such as an intubation tube or endoscope 26, the exhalation scoop 12 can be flexed or pushed by the device in the nominal "y" direction, providing access to the patient's mouth as shown in FIG. 3.

Figure 4:
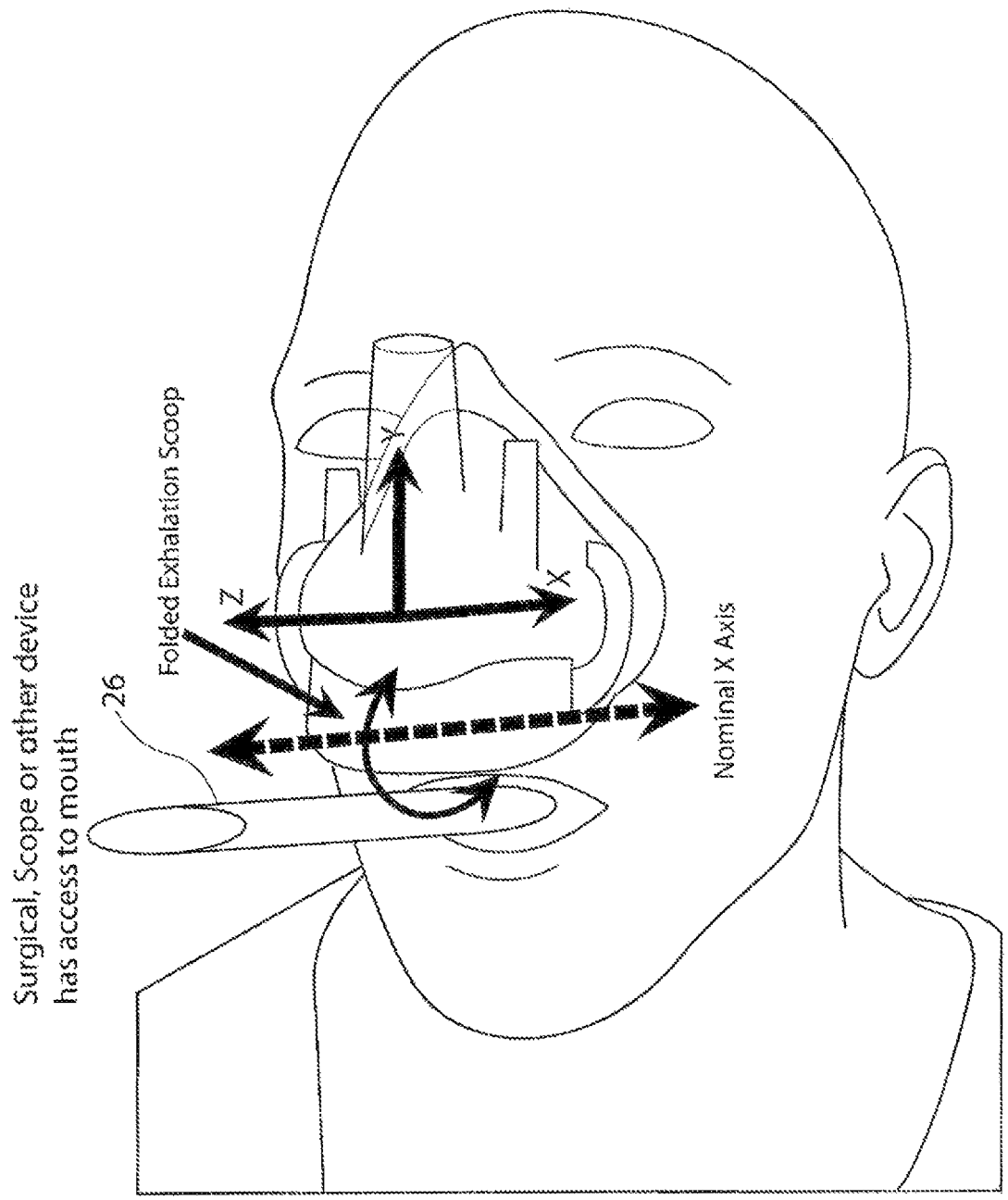
FIG. 4 is a view similar to FIG. 2, showing a nasal mask with an exhalation scoop folded out of the way to provide oral access.

Another benefit of one flexible exhalation scoop 12 design is that if the surgeon requires access to the patient's mouth, there exists a bi-stable condition where the scoop 12 overlies the upper lip and/or mouth of the patient, as shown in FIG. 2, or the scoop 12 can be folded over itself about the nominal "X" axis and remain stable with the scoop 12 no longer covering the mouth as shown in FIG. 4. This allows access to the patient's mouth as shown, and nasal Et $CO_2$ can still be collected. Once the endoscope 26 or other device is removed from the patient's mouth, should the clinician decide to continue collecting oral Et $CO_2$ samples, the flexible exhalation scoop 12 can be unfolded about the "X" axis, again covering the patient's mouth as in FIG. 2.

Completing the nasal mask are tabs and/or eyelets 30 for attaching one or more head straps (not shown).

Figure 5:
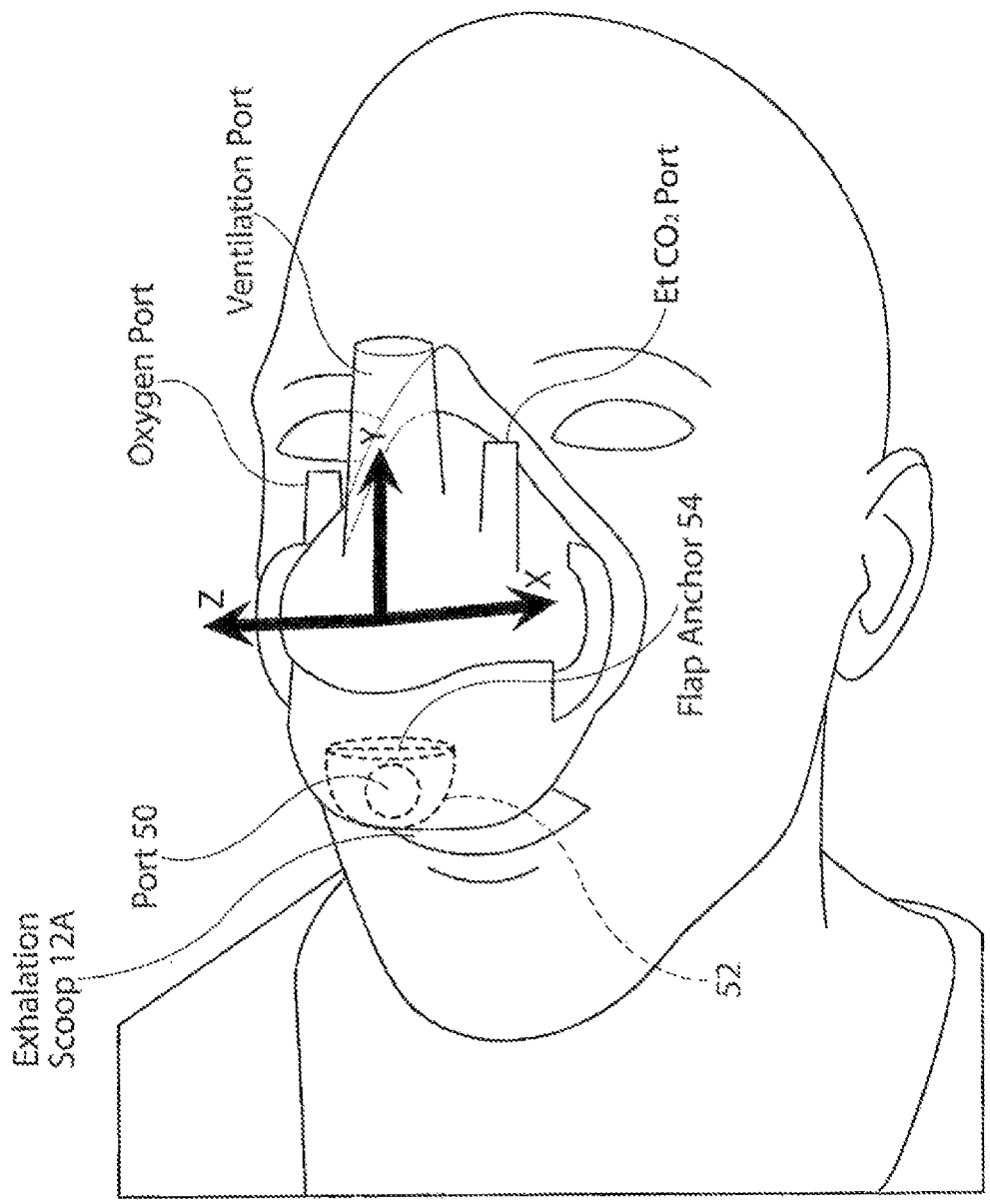
FIG. 5 is a perspective view of a nasal mask with an exhalation scoop showing an alternative method of gaining access to the mouth in accordance with a second embodiment of the present invention.
Figure 6:
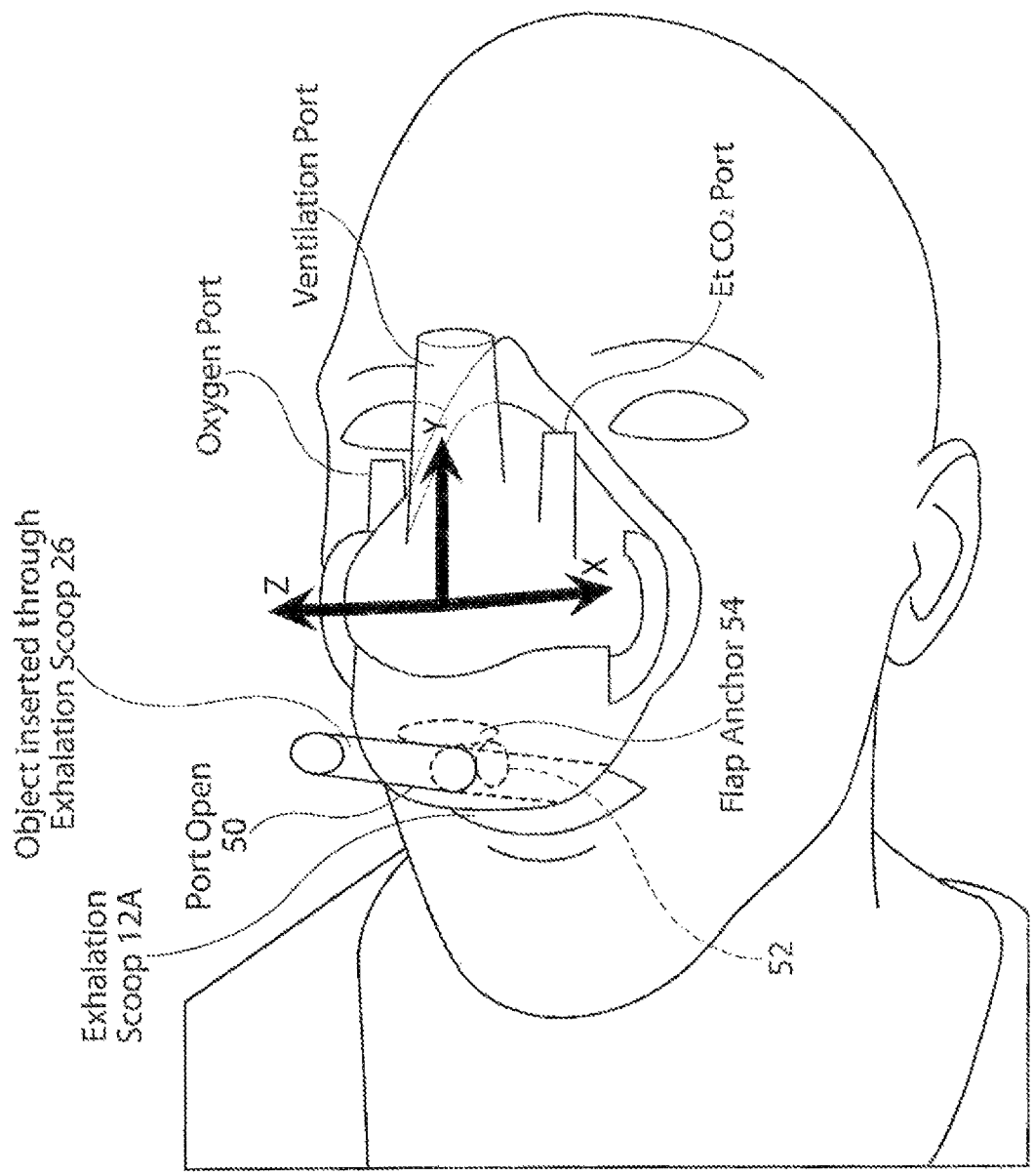
FIG. 6 is a view similar to FIG. 5 showing how oral access is achieved using the exhalation scoop of FIG. 5.

Referring to FIGS. 5 and 6, in an alternative embodiment of the invention, the exhalation scoop 12A includes a circular aperture 50 covered by a flap 52 attached to the inside of the exhalation scoop 12A at anchor 54. Exhalation scoop 12A is similar in shape to the exhalation scoop 12 of FIGS. 1-4, but need not be made of as flexible materials. Flap 52 and anchor 54 are shown in phantom since they are on the inside of scoop 12A. Flap 50 is in a normally closed position, and is held against the inside surface of scoop 12A by positive pressure within the mask, when the mask is worn by a patient.

FIG. 6 shows a functional device such as an intubation tube or endoscope 26 inserted through aperture 50, pushing flap 52 aside whereby to permit access to the patient's mouth, while permitting continual end-tidal sampling, etc. Flap 50 is flexible so as to substantially seal around the functional device. When the functional tool 26 is removed, the aperture 50 is again sealed by flap 50.

Figure 7:
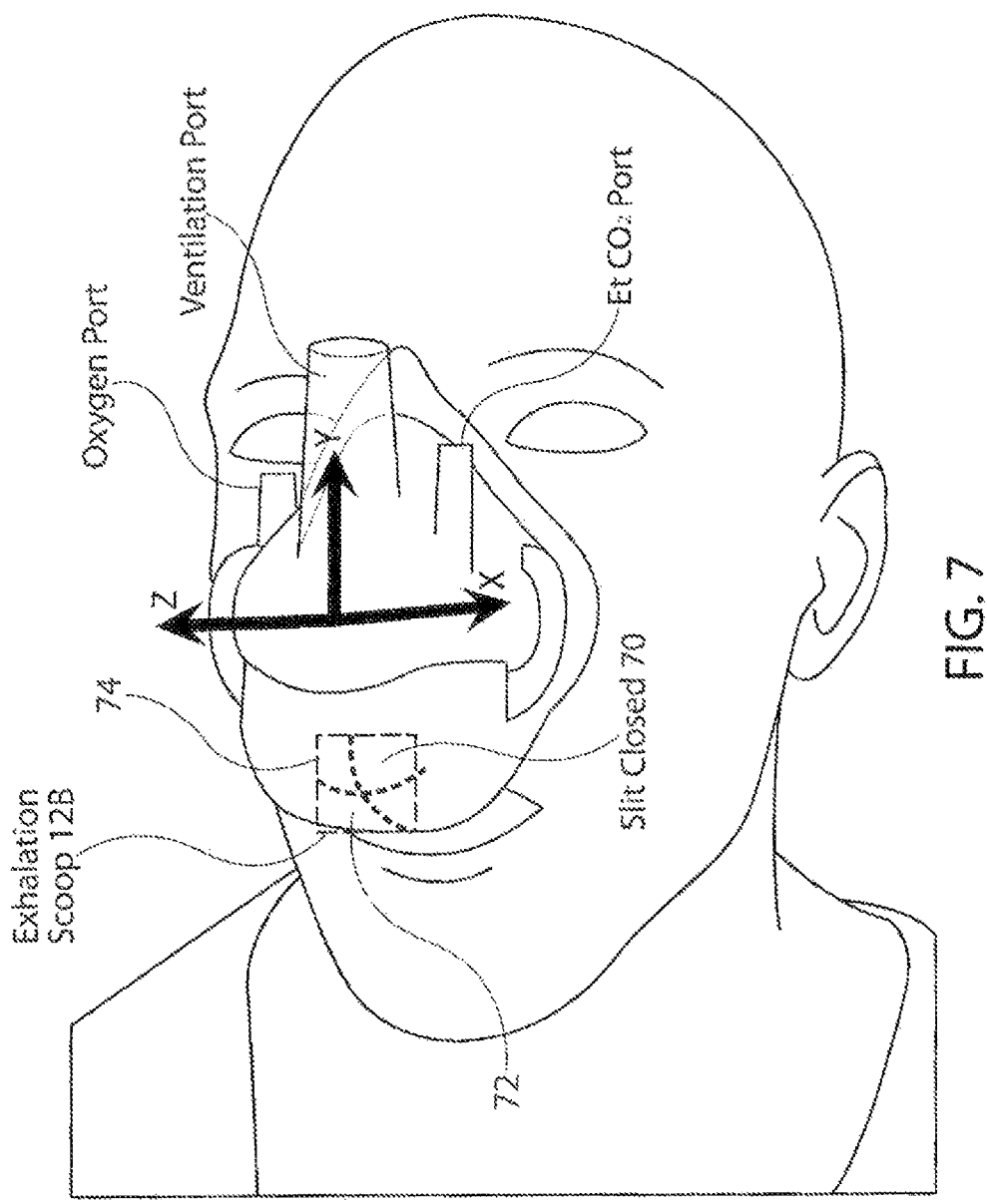
FIG. 7 is a view similar to FIG. 5 of a third embodiment of the invention.

In another embodiment, shown in FIG. 7, aperture 50 is replaced by a slip 70 which is backed by flexible flap 72 anchored at 74 to the inside of the exhalation scoop 12B. Similar to port 50, slit 70 permits insertion of a functional device through the exhalation scoop, giving access to the patient's mouth, while leaving the exhalation scoop in place so as to permit continued end-tidal $CO_2$ sampling, etc.

Note with respect to the embodiments of FIGS. 5-6 and 7, any geometric shape may be used for the aperture, the slits and the flap so as to permit passage of a laryngoscope, endotracheal tube, endoscope or other functional device to pass through the exhalation scoop, while leaving the exhalation scoop in place for continued end-tidal $CO_2$ monitoring, etc. Due to the flexibility of the flap, the flap essentially seals around the functional tool and allows for continued collection of orally expelled $CO_2$. When the tool is removed from the scoop, the flap again closes off the aperture or slits.

Yet another embodiment of the invention is shown in FIGS. 8A-8C. In this latter embodiment, the Et $CO_2$ port has a luer connection 80, thus providing the Et $CO_2$ port the ability to interface with other devices, having a luer interface connection 82 such as a syringe 84. Thus, the Et $CO_2$ port can be utilized to deliver fluids, or gases, including sedatives such as lidocaine, contained in a syringe. FIGS. 8A-8B show a fluid-filled syringe 84 being connected to the Et $CO_2$ port and FIG. 8C shows the syringe 84 being compressed, with the fluid being expelled into the interior of the mask. Gasses, such as $O_2$, that flow through either the $O_2$ port, the ventilation port 86, or both, will mix with the expressed fluid, nebulizing it where it is then inhaled by the patient.

Referring again to FIG. 2, as noted supra, mask 10 also includes a gas sampling device (shown in phantom at 16) in the form of suction attached to an end-tidal ("ET") $CO_2$ port 18 and adapted for drawing gas samples from both the oral and nasal exhalations of the patient. One opening 20 of the $EtCO_2$ manifold is behind the exhalation scoop 12 to overlie the upper lip of a patient, when the mask is worn by a patient, on the exterior of the nasal mask 10, where a negative pressure (pressure less than atmospheric pressure) is created by gas sampling device 16. A second opening 22 of the manifold is below the nares on the interior of the nasal mask where a negative pressure is also created by the gas sampling device 16. When the patient exhales, oral and nasal exhalation are collected through openings 20, 22 and proceed through the manifold and exit the $EtCO_2$ port that is connected to the gas sampling device 16 that provided the negative pressure. Concentration levels of the gas, such as $CO_2$ are then measured by gas sampling device 16.

Figure 11:
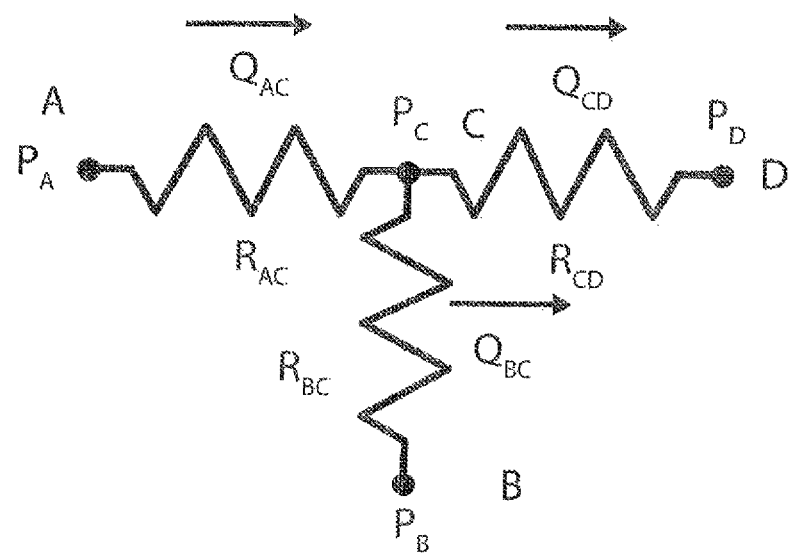
FIG. 11 is a fluid flow schematic in accordance with the FIG. 2 mask.

Referring also to FIGS. 9-11, in use oral exhalation enters the $CO_2$ port through a single opening, hole 20, and nasal exhalation enters the $CO_2$ port through a single opening, hole 30, as shown in FIG. 2. The $CO_2$ port is connected to a $CO_2$ monitoring device that creates suction, collecting the exhalation sample by a sampling line. The mask operates in an unpressurized configuration here oxygen is supplied through the $O_2$ port 25 and the ventilation port 23 is open to the atmosphere where both the oxygen and exhalation of $CO_2$ escape, as well as a pressurized configuration where the oxygen enters the mask through the ventilation port and also, optionally, the oxygen port. Exhalation of the $CO_2$ and oxygen then exits through the ventilation port 23 that is connected to either an anesthesia machine, a ventilator, a CPAP machine or a ventilation bag such as one on a hyperinflation system.

Volumetric flow through a pipe, Q, is governed by the fluid dynamic laws shown in Equations 1-5.

$$Q = \pi \phi^2 V / 4 \quad \text{Eq. 1}$$

$$\Delta P = \rho f L V^2 / 2\phi \quad \text{Eq. 2}$$

$$\Delta P = (8\rho f L / \pi^2 \phi^5) Q^2 \quad \text{Eq. 3}$$

$$R^2 = (8\rho f L / \pi^2 \phi^5) \quad \text{Eq. 4}$$

$$Q = \Delta P^{1/2} R \quad \text{Eq. 5}$$

wherein:
Q=Volumetric flow rate ($m^3$/min)
$\rho$=fluid density (kg/$m^3$)
$\phi$=pipe diameter (m)
V=fluid velocity (m/min)
$\Delta P$=Differential pressure between two points (Pa)
f=friction factor for pipe
L=pipe length (m)
R=pipe resistance ($Pa^{1/2}$-min/$m^3$)

The fluid flow model for the current mask 10 shown in FIGS. 2 and 9-11 has 4 node points with respective pressure and flow rates defined as follows:

Node point A, Entrance of hole 20 that is the oral opening into the $CO_2$ Port.
  Hole 20 diameter, $\phi_a = \phi_{CO2\ Port}$
  Pressure at hole 20, $P_A$
  Volumetric oral exhalation flow through hole 20, $Q_{AC}$
  Pipe resistance from Node A to Node C, $R_{AC}$
  Length of pipe from Node A to Node C, $L_{AC}$
Node point B, Entrance of hole 22 that is the nasal opening into the $CO_2$ Port.
  Hole 22 diameter, $\phi_b$
  Pressure at hole 22, $P_B$
  Volumetric nasal exhalation flow through hole 22, $Q_{BC}$
  Pipe resistance from Node B to Node C, $R_{BC}$
  Length of pipe from Node B to Node C, $L_{BC}$
Node point C, Interior of $CO_2$ Port adjacent to exit of hole 22 into $CO_2$ Port
  $CO_2$ Port diameter, $\phi_{CO2\ Port}$
  Pressure at Node C, $P_C$
  Volumetric flow through Node C, $Q_{CD}$
  Pipe resistance from Node C to Node D, $R_{CD}$
  Length of pipe from Node C to Node D, $L_{CD}$
Node point D, Exit of $CO_2$ Port (Connects to $CO_2$ Sample line)
  $CO_2$ Port diameter, $\phi_{CO2\ Port}$
  Pressure at Node D, $P_D$
  Volumetric flow through Node D, $Q_{CD}$
Flow between each of the Node points is defined as follows:

$$Q_{AC} + Q_{BC} = Q_{CD} \quad \text{Eq. 6}$$

$$Q_{AC} = (P_A - P_C)^{1/2} / R_{AC} \quad \text{Eq. 7}$$

$$Q_{BC} = (P_B - P_C)^{1/2} / R_{BC} \quad \text{Eq. 8}$$

$$Q_{CD} = (P_C - P_D)^{1/2} / R_{CD} \quad \text{Eq. 9}$$

Ideally, the flow from the oral and nasal exhalation, $Q_{AC}$ and $Q_{BC}$, are equal in order to measure exhaled $CO_2$. In an unpressurized configuration, $P_A$ and $P_B$ are both approximately equal and equal to the atmospheric pressure. In such configuration, the associated resistance between nodes, $R_{AC}$ and $R_{BC}$ would be designed to be equal by properly configuring the associated pipe diameters and pipe lengths. The challenge is that in a pressurized configuration, the nasal portion of the mask, PB, is pressurized to a nominal value of 10-15 CM $H_2O$ relative to the atmosphere and $P_A$. In such configuration, $R_{BC}$ will need to be proportionally larger than $R_{AC}$ in order to have $Q_{AC}$ equal $Q_{BC}$. If $R_{BC}$ were not increased, the $Q_{BC}$ would be larger than $Q_{AC}$. In order to maintain substantially equal oral and nasal flow for $CO_2$ sampling for both the unpressurized and pressurized configurations, $R_{BC}$ must vary as a function of $P_B$ in order to maintain equal flow.

As used herein the terms "substantially balancing flow" and "substantially constant flow" are used interchangeably, and mean a flow of within about volume 10%, preferably within about volume 5%, more preferably within about volume 2-3%.

Figure 12C:
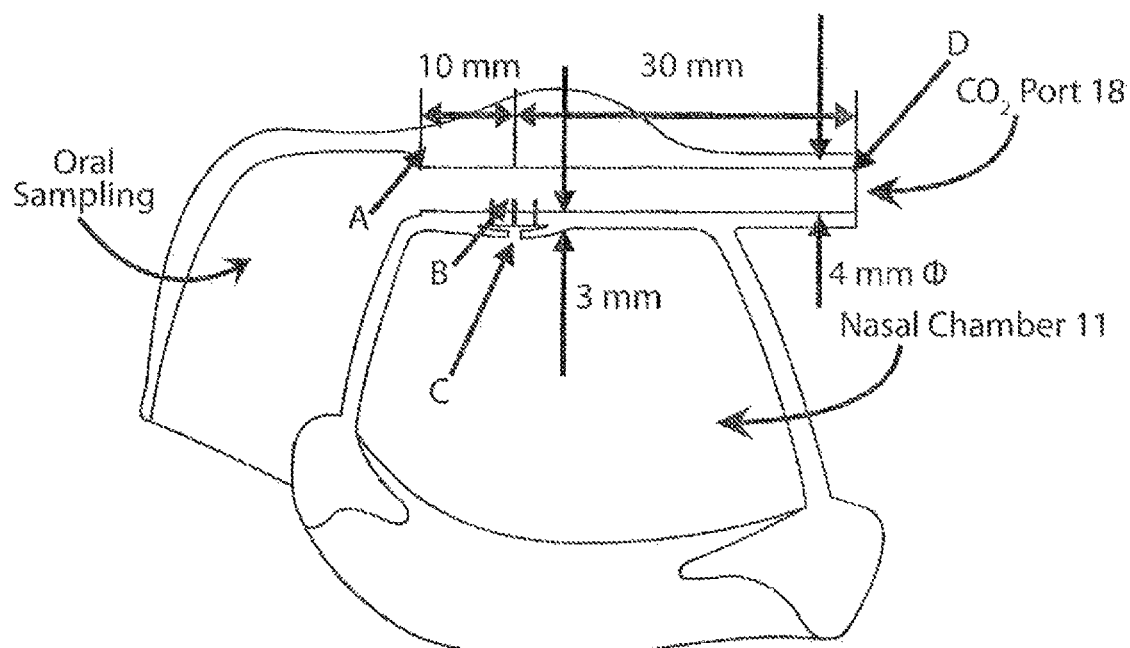
FIG. 12C is a side elevational view, in cross section, of the nasal mask of FIG. 12A.

A preferred embodiment of a pressure-based flow resistor is illustrated in FIGS. 12A-12C. In this embodiment, the nasal mask 100, which is similar to mask 10 described above, includes a manifold 102 with two or more holes 104, 106 connecting nasal chamber of the mask to a $CO_2$ port 18. Referring also to FIGS. 13A and 13B a membrane disk 112 having an opening 114 is aligned over a hole 116 which covers the manifold 102 where under a given pressure, $P_B$, nasal exhalation can travel through the hole 114 of the manifold, hole 116, as well as a hole 118 into the $CO_2$ port 18. As pressure increases, to $P_{BCrit}$, the membrane disk 112 deflects in the Z direction by moving up by a distance $\delta Z$. At that point, flow from the nasal chamber 11 to hole 118 is blocked and can only travel through hole 116. As a result, flow resistance from the nasal chamber 11 to the $CO_2$ port 18 $R_{BC}$, is increased. Hole 118 and hole 116 geometry can be selected so that when the membrane disc 112 has deflected an amount less than $\delta Z$, the flow, $Z_{BC}$, as defined by $(PB-PC)^{1/2}/R_{BC}$ is nominally constant and made substantially equal to Om from Oral exhalation. As a result, sampling flow is substantially equalized.

Various changes may be made in the above without departing from the spirit and scope of the invention.

What is claimed:

1. A nasal mask comprising:
   an inner surface forming a nasal chamber;
   a ventilation port that extends from an upper portion of the nasal mask in a first direction;
   an end-tidal $CO_2$ port that extends from the upper portion of the nasal mask and comprises an opening adjacent a lower portion of the nasal mask; and
   an exhalation scoop fixed adjacent the lower portion of the nasal mask and adapted to overlie an upper lip of a patient when the nasal mask is worn;
   wherein the opening is located behind the exhalation scoop for sampling $CO_2$ expelled from a mouth of the patient, and the exhalation scoop is formed of a material that is flexible relative to a material that defines the nasal chamber such that the exhalation scoop is adapted to be folded back in the first direction toward the nasal chamber to permit access to the mouth of the patient.

2. The nasal mask of claim 1, wherein the end-tidal $CO_2$ port extends from the upper portion of the nasal mask in the first direction.

3. The nasal mask of claim 1, wherein the end-tidal $CO_2$ port comprises another opening located in the nasal chamber to underlie a nare of the patient for sampling exhaled $CO_2$ expelled from a nose of the patient.

4. The nasal mask of claim 1, wherein the ventilation port is configured to connect with any of an anesthesia machine, a ventilation machine, or a hyperinflation bag.

5. The nasal mask of claim 1, further comprising an oxygen port configured to connect with an oxygen source for supplying oxygen to the nasal chamber.

6. The nasal mask of claim 5, wherein the oxygen port extends from the upper portion of the nasal mask in the first direction.

7. The nasal mask of claim 1, wherein the material of the exhalation scoop is formed of a material having a Shore 00 Durometer Hardness of 0020 to 0050.

8. The nasal mask of claim 1, wherein the material of the exhalation scoop is formed of a material having a Shore A Hardness selected from 2-10 or 3-7.

9. The nasal mask of claim 1, further comprising a groove in an outer surface of the nasal mask, wherein the exhalation scoop comprises a lip configured to fit in the groove.

10. The nasal mask of claim 1, wherein the exhalation scoop is integrally formed with the nasal mask.

11. The nasal mask of claim 1, wherein the exhalation scoop is configured to be folded around an axis that extends in a second direction, and wherein the second direction is transverse relative to the first direction.

12. A method for ventilating a patient, comprising:
    providing a nasal mask having an inner surface forming a nasal chamber, a ventilation port that extends from an upper portion of the nasal mask in a first direction, an end-tidal $CO_2$ port that extends from the upper portion of the nasal mask and comprises an opening adjacent a lower portion of the nasal mask, and an exhalation scoop fixed adjacent the lower portion of the nasal mask and adapted to overlie an upper lip of the patient when the nasal mask is worn, such that the opening is located behind the exhalation scoop;
    connecting the ventilation port to any of an anesthesia machine, a ventilation machine, or a hyperinflation bag;
    folding the exhalation scoop back in the first direction toward the nasal chamber to permit access to a mouth of the patient; and
    monitoring end-tidal $CO_2$ by sampling exhaled $CO_2$ expelled from the mouth of the patient into the opening.

13. The method of claim 12, monitoring end-tidal $CO_2$ by sampling $CO_2$ expelled from a nare of the patient into another opening of the end-tidal $CO_2$ port located in the nasal chamber.

14. The method of claim 12, further comprising connecting an oxygen port of said nasal mask to an oxygen source for supplying oxygen to the nasal chamber of the nasal mask.

15. The method of claim 12, wherein folding the exhalation scoop back in the first direction comprises folding the exhalation scoop around an axis that extends in a second direction, and wherein the second direction is transverse relative to the first direction.

16. The method of claim 12, further comprising unfolding the exhalation scoop in a second direction away from the nasal chamber to permit access to the mouth of the patient, wherein the second direction is opposite to the first direction.

17. The method of claim 12, further comprising connecting the end-tidal $CO_2$ port of the nasal mask to a gas sampling device.

* * * * *